US007628982B2

(12) United States Patent  (10) Patent No.: US 7,628,982 B2
Klaviniskis et al. (45) Date of Patent: Dec. 8, 2009

(54) **COMPOSITION AND CORRESPONDING METHOD OF USING SPORES OF *BACILLUS SUBTILIS* TO STIMULATE AND/OR ENHANCE IMMUNE RESPONSE IN MAMMALS**

(75) Inventors: Linda Sylvia Klaviniskis, London (GB); Andrew Graham Colin Barnes, London (GB)

(73) Assignee: King's College London (GB)

( * ) Notice: Subject to any disclaimer, the term of this patent is extended or adjusted under 35 U.S.C. 154(b) by 0 days.

(21) Appl. No.: 10/309,635

(22) Filed: Dec. 4, 2002

(65) Prior Publication Data

US 2003/0147923 A1 Aug. 7, 2003

(30) Foreign Application Priority Data

Dec. 21, 2001 (GB) ................. 0130789.1

(51) Int. Cl.
*A01N 63/00* (2006.01)
*A01N 65/00* (2006.01)
*A61K 48/00* (2006.01)
*A61K 39/38* (2006.01)
*A61K 39/07* (2006.01)
*A61K 45/00* (2006.01)

(52) U.S. Cl. .................. 424/93.462; 424/246.1; 424/93.46; 424/93.1; 424/93.4; 424/184.1; 424/278.1

(58) Field of Classification Search ................ 424/93.2, 424/246.1, 184.1, 93.462; 514/44
See application file for complete search history.

(56) References Cited

U.S. PATENT DOCUMENTS

| 5,800,821 | A | 9/1998 | Acheson et al. |
| 2002/0150594 | A1 | 10/2002 | Goldman et al. |
| 2003/0147923 | A1* | 8/2003 | Klaviniskis et al. ...... 424/246.1 |

FOREIGN PATENT DOCUMENTS

| GB | 2 370 772 A | 7/2002 |
| WO | WO 02/00232 A2 | 1/2002 |
| WO | WO 03/055513 A2 * | 7/2003 |
| WO | WO 03/074682 A1 * | 9/2003 |

OTHER PUBLICATIONS

Welkos et al, Microbial Pathogenesis, 1988, 5:127-139.*
Duc et al, Expert Opinion Biol. Ther., 2003, 3/8:1263-1270.*
Cutting, In: Bacterial Spore Formers, editors Ricca et al, 2004, pp. 201-206.*
Himanen et al, Vaccine, 1993, 11/9:970-973.*
Saris et al, FEMS Microbiology Letters, 1990, 68:143-148.*
Ivins et al, Infection and Immunity, 1986, 54/2:537-542.*
Gregoriadis, Immunomethods, 1994, 4:210-216.*
Acheson et al, Vaccines 97, 1997, pp. 179-184.*
Barnes et al, Current Opinion in Molecular Therapeutics, 2000, 2/1:87-93.*
Gursel et al, Drug Targeting and Delivery, 1995, 6:35-50.*
Idanpaan-Heikkila et al, Vaccine. 1996, 14/9:886-891.*
Muttilianen et al, Microbial Pathogenesis, 1995, 18:365-371.*
Duc et al, Infection and Immunity, 2003, 71/5:2810-2818.*
Ivins et al, Infection and Immunity, 1990, 58/2:303-308.*
Gregoriadis et al, Methods, 1999, 19:156-162.*
Baillie et al, FEMS Microbiology Letters, 1998, 163:43-47.*
Oggioni et al, Vaccine, 2003, 21:S2/96-S2/101.*
Duc et al, Vaccine, 2003, 21:4215-4224.*
Mauriello et al, Vaccine, 2004, 22:1177-1187.*
Duc et al, Vaccine, 2004, 22:1873-1885.*
Ciabattini et al, Vaccine, 2004, 22:4139-4143.*
Atrih et al, J. Bacteriology, Sep. 1998, 180/17:4603-4612.*
Nicholson et al, Microbiology and Molecular Biology Reviews, Sep. 2000, 64/3:548-572.*
Novelli et al, Chemioterapia, Jun. 1984, 3/3:152-155.*
Clark Burton et al, J. Environmental Monitoring, 2005, 7/5:475-480.*
Gialdroni-Grassi et al, Int. Archs. Allergy Appl. Immunol., 1985, 76/Suppl. 1:119-127.*
Isticato et al, J. Bacteriology, Nov. 2001, 183/21:6294-6301.*
Uyen et al, Vaccine, 2007, 25:356-365.*
Paccez et al, Vaccine, 2006, 24:2935-2943.*
Duc et al, Vaccine, 2007, 25:346-355.*
Zhou et al, Vaccine, 2008, 26:1817-1825.*
Buchanan, J. Bacteriology, Nov. 1987, 169/11:5301-5303.*
Folmsbee et al, Applied and Environmental Microbiology, Sep. 2004, 70/9:5252-5257.*
Shaver et al, Molecular Microbiology, 2001, 42/1:101-109.*

(Continued)

*Primary Examiner*—N. M Minnifield
(74) *Attorney, Agent, or Firm*—Joseph T. Leone, Esq.; DeWitt Ross & Stevens S.C.

(57) ABSTRACT

Disclosed is a composition for administration to a human or animal subject, the composition containing spores of *Bacillus subtilis* in an amount effective to stimulate immune responsiveness in the subject. The spores have an adjuvant, immunomodulatory, immune potentiation, or dendritic cell maturation effect, or a combination thereof Also disclosed is a method of boosting an immune response in an animal subject by administering *B. subtilis* spores to an animal or human subject. Further disclosed is a vaccine containing *B. subtilis* spores, in the presence or absence of an antigen.

11 Claims, 20 Drawing Sheets

OTHER PUBLICATIONS

Figure 1:
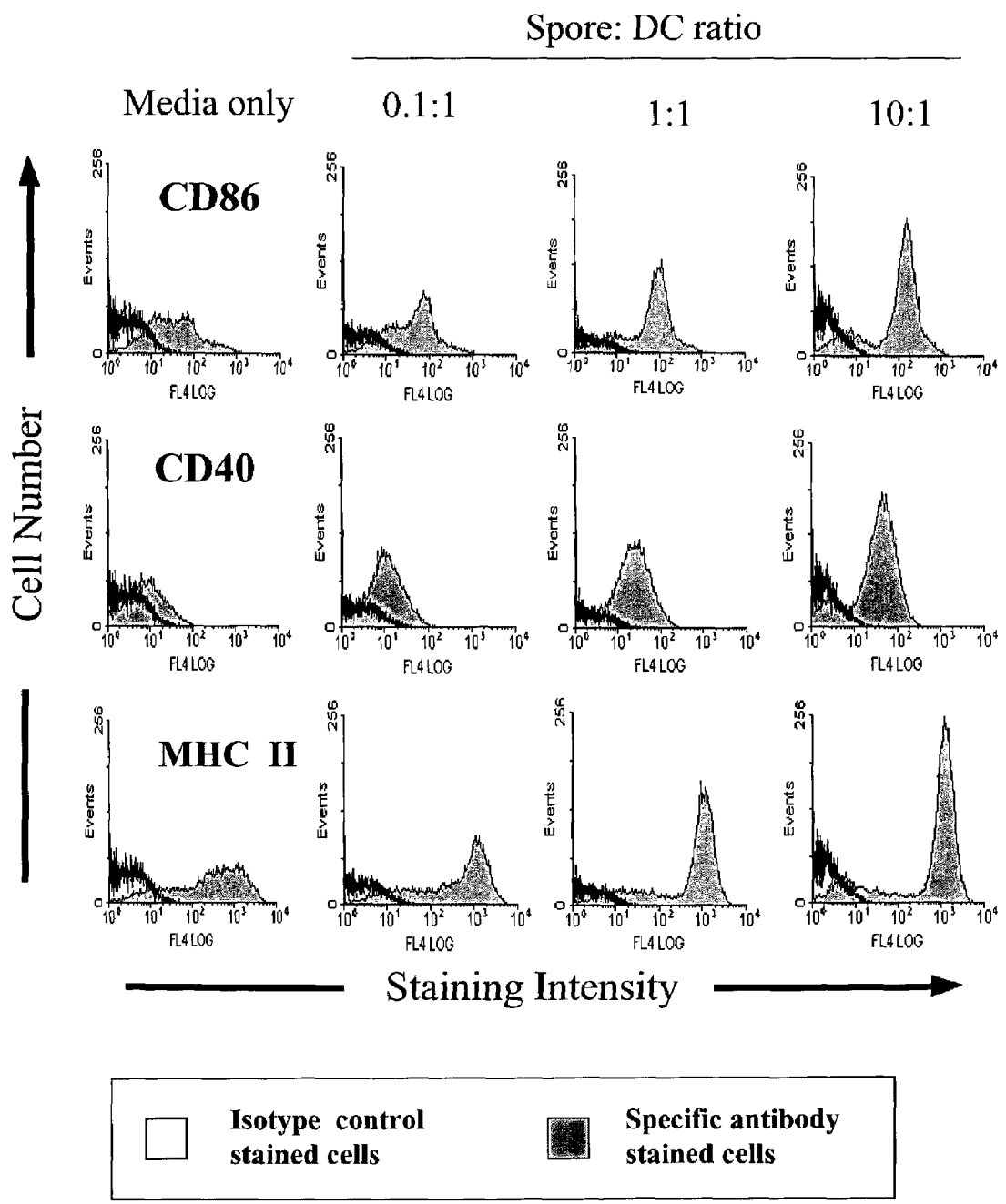

Banchereau et al. 2000. Immunobiology of dendritic cells. *Ann Rev Immunol.* 18:767-811.

Ben-Yedidia et al.. 1998. Efficacy of anti-influenza peptide vaccine in aged mice. *Mech. Aging Dev.* 104(1):11-23.

Bluestone J.A. 1995. New perspectives of CD28-B7-mediated T cell costimulation. *Immunity.* 2(6):555-9.

Caruso et al. 1993. Expression of activation markers on peripheral blood lymphocytes following oral administration of *Bacillus subtilis* spores. *Int J. Immunopharmac.* 15:87-92.

Chambers C, 2001. The expanding world of co-stimulation: the two signal model revisited. *Trends in Imunol.* 22:217-223.

Chintalacharuvu et al. 2001. T cell cytokines determine the severity of experimental IgA nephropathy by regulating IgA glycosylation. *Clin Exp Immunol.* 126(2):326-333.

Cipriandi et al. 1986a. Effects of an adjunctive treatment with *Bacillus subtilis* for food allergy. *Chemoterapia.* 5: 408-410.

Cipriandi et al.. 1986b. In vitro effects of *Bacilus subtilis* on the immune response. *Chemoterapia.* 5:404-407.

Cohn, F. 1872. "Untersuchungen uber Bakterien." Beitrage zur Biologie der Pflanzen, 1875 1 (Heft 2) 1:127-224.

Danengerg et al. 1997. Dehydroepiandrosterone treatment is not beneficial to the immune response to influenza in elderly subjects. *J. Clin Endroclinol Metab.* 82:2911-2914.

Davenport et al.. 1968. Lack of adjuvant effect of AIPO on purified influenza virus hemagglutinins in man.. *J Immunol.* 100(5):1139-40.

Fiorini et al.. 1985. *Bacillus subtillis* selectively stimulates the synthesis of membrane bpoound and secreted IgA. *Chemoterapia.* 4: 310-312.

Fujihashi et al. 2000. Mucosal vacination and immune responses in the elderly. Vacine 18: 1675-1680.

Glezen et al. 1999. Maternal immunization. *Clin Infect Dis* Feb;28(2):219-24.

Green et al. SM. 1999. Characterization of *Bacillus* species used for oral bacteriotherapy and bacterioprophylaxis of gastrointestinal disorders. *Appl. Environ. Microbiol.* 65:4288-89.

Hoa et al. 2000. Characterization of *Bacillus* species used for oral bacteriotherapy and bacterioprophylaxis of gastrointestinal disorders. *Appl. Environ. Microbiol.* 66: 5241-47.

Hodge et al.. 2001. Immunoglobulin A (IgA) responses and IgE-associated inflammation along the respiratory tract after mucosal but not systemic immunization. *Infect Immun* April, 69(4):2328-38.

Houba et al.. 1992. Protodyne: an immunostimulatory protein component, prepared from gram-positive *Bacillus subtilis*. *Dev. Biol. Stand.* 77: 1211-28.

Hinmanen et al. 1993. Biological activities of lipoteichoic acid and peptidoglycan-tichoic acid of *B. subtilis* 168 9Marburg). *J. Gen. Microbiol.* 139:2659-2665.

Johnen et al. 2001. Long-term tumour growth suppression in mice immunized with naked DNA of the human tumour antigen mucin (MUCi). *Cancer Immunol. Immunother.* 50:356-360.

Kaliński et al. 1999. T-cell priming by type-i and type-2 polarized dendritic cells: the concept of a third signal. *Immunol Today* December;20(12):561-7.

Langenkamp et al. 2000. Kinetics of dendritic cell activation: impact on priming of TH1, TH2 and nonpolarized T cells. *Nat Immunol.* (4):311-16.

Lyden et al. 2001. The Fc receptor for IgG expressed in the villus endothelium of human placenta is Fc gamma RIIb2. *J Immunol* 166(6):3882-89.

Maidak et al. 2000. The RDP (Ribosomal Database Project) continues. *Nucleic Acids Res*, 28(1): 173-74.

Malkiel et al. 1971. The adjuvant activity of bacillus subtilis and subtiliis. *J. Allergy.Clin. Immunol.* 48:220-223.

Manning et al. 2001. CpG DNA functions as an effective adjuvant for the induction of immune responses in aged mice. *Exp. Geront.* 37:107-126.

Mishell B.B. and Shiigi S.M. eds. 1980. Selected methods in cellular immunology. W.H. Freeman and Company, New York., pp. 3-5.

Mazza P. 1994. The use of *Bacillus subtilis* as an anti-diarrhoeal microorganism. *Boll. Chim. Farm.* 133:3-18.

Morelli et al..2001. Cytokine production by mouse myeloid dendritic cells in relation to differentiation and terminal maturation induced by lipopolysaccharide or CD40 ligation *Blood.*, 98(5):1512-23.

Nagao et al. 2001. Elevated levels and different repertoire profile of colostral anti-LPS antibodies may have a significant role in compensating newborn immunity. *Scand J Immunol* 53(6):602-9.

Okoko et al. 2001. The influence of prematurity and low birthweight on transplacental antibody transfer in a rural West African population. *Trop Med Int Health* Jul. 2001;6(7):529-34.

Parissi-Crivelli et al. 2000. Recognition of enteropathogenic *Escherichia coli* virulence determinants by human colostrum and serum antibodies. *J Clin Microbiol* 38(7):2696-700.

Rappuoli et al. 1999. Structure and mucosal adjuvanticity of cholera and *Escherichia coli* heat-labile enterotoxins, *Immunology Today* 20:493-499.

Reis e Sousa et al.. 1997. In vivo microbial stimulationinduces rapid CD40 ligand-independent production of Interleukin 12 by dendritic cells and their residtribution to T cell areas., *J. Exp. Med.* 186:1819-1829.

Senesi et al.. 2001. Molecular characterization and identification of *Bacillus clausii* strains marketed for use in oral bacteriotheraphy. *Appl. Environ. Microbiol.* 67:834-839.

Sneath, P.H.A. 1986. Endospore forming gram positive rods and cocci. Bergey's Manual of Systemic Bacteriology. (Ed. Holt J.G.) Williams and Wilkins. Baltimore. vol. 2, Section 13, 1130.

Spencer et al. 1996. Dysregulation of IL-10 production with aging: possible linkage to th age-asociated decline in DHEA and its sulphates derivative. *Exp. Gerontol*, 31:393-408.

Svensson 1997. Bone marrow-derived dendritic cells can process bacteria for MHC-I and MHC-II presentation to T cells. *J Immunol.* 158(9):4229-36.

Tortorella et al. 2002. APC-dependant impairment of T cell proliferation in aging: role of CD28- and IL-12/IL-15 mediated signaling. *Mech. Aging Dev.* 123:1389-1392.

van Ginkel et al. 2000. Cutting Edge: The mucosal adjuvant cholera toxin redirects vaccine proteins into olfactory tissues. *J. Immunol.* 165:4778-4782.

\* cited by examiner

COMPOSITION AND CORRESPONDING METHOD OF USING SPORES OF *BACILLUS SUBTILIS* TO STIMULATE AND/OR ENHANCE IMMUNE RESPONSE IN MAMMALS

PRIORITY CLAIM

Priority is hereby claimed to co-pending Great Britain patent application Serial No. 0130789.1, filed Dec. 21, 2001, the entirety of which is incorporated herein by reference.

FIELD OF THE INVENTION

This invention relates to materials having adjuvant, immunomodulatory, immunopotentiatory or innate stimulatory effects for use in vaccines or as an immunomodulator/booster of the immune system. The invention is directed to the use of such materials in prophylactic and therapeutic vaccines for human and veterinary (companion animal, poultry, commercial livestock and fisheries) use against infectious disease, cancer and allergic disease (for all routes of delivery, systemic and mucosal), as an immunepotentiator to boost maternal antibodies for passive transfer to babies, or in the elderly to boost ageing immune systems, and as a stand alone innate stimulator of dendritic cells (DC) in vitro (for therapeutic infusion) or in vivo to induce a rapid innate immune response against exposure to microbes, which has application as a generic prophylactic or neo-exposure therapeutic against biological warfare or as a generic prophylactic or neo-exposure holiday therapeutic immunepotentiator.

BACKGROUND OF THE INVENTION

Concern over the safety of inactivated or attenuated vaccines, in terms of administration to immunocompromised individuals and possible reversion to virulence has led to the development of subunit vaccines (composed of purified antigenic components of a micro-organism), DNA vaccines and also replication defective vaccine vectors. While these approaches are devoid of safety concerns, the purified proteins are generally less immunogenic than when expressed from a replicating organism. Furthermore, DNA vaccines and replication defective vaccine vectors encoding the gene of interest to stimulate the immune system generally express lower levels of antigen than replicating microorganisms. Thus multiple doses are required, which is uneconomic. For these vaccines to reach their full potential requires the incorporation of adjuvants to boost the immune response to the vaccine components.

Efficient stimulation of immune responses occurs when antigens are presented by potent professional antigen presenting cells. These consist primarily of DC's, present at the epithelial surfaces of the body, which form a surveillance system for recognition of foreign antigens. DC's are now recognized to take up and process antigens and present antigenic peptides in the context of Major Histocompatibility (MHC) molecules for recognition by T-lymphocytes (Banchereau et al 2000). However, besides recognition of foreign antigens, T lymphocytes require additional signals to become fully active (Bluestone, 1995). Costimulatory molecules (exemplified by CD80, CD86 and CD40) expressed on the surface of activated DC's provide these signals when they interact with their receptors on the T cell surface (Chambers C, 2001).

Replicating microorganisms (but not purified proteins or replication defective vaccine vectors) efficiently stimulate DC's to upregulate these costimulatory molecules and provide signals that induce strong immune responses. Thus it is now understood that one of the principal activities of adjuvants resides in their ability to mature DC, including upregulation of MHC class I and II and DC costimulatory molecules, which provide potent signals for the full activation of responding T (and also B) cells.

DCs are also recognized to play a fundamental role in determining the type of immune responses generated through the production of cytokines which regulate which T helper (Th) cell subset is primed (Lanzavecchia et al 2001). DC production of interleukins (IL-12, tumour necrosis factor alpha [TNF-α] and IL-4) is required to generate a balanced immune response. IL-12 and TNF-α production is critical in the generation of Th1 responses, the generation of CD8 T-cell responses, the production of IgG2a, IgG2b and IgG3 antibodies and recruitment of immune cells into the site of vaccine administration. IL-4 production is required to generate Th2 responses and stimulate B-cells to produce antibodies. Although IL-4 promotes Th2 responses it does not inhibit IL-12 in the generation of Th1 responses (Kalinski 1999). In the absence of IL-12, adjuvant induced production of IL-4 can result in not only IgG1 but also IgE which is associated with allergic disease (Hodge 2001) and serum IgA that can cause IgA nephropathy (Chintalacharuvu 2001).

Aluminium salts (alum) are the only universally licensed adjuvant for human use. However, they have the disadvantage of inducing allergic immunoglobulin-E (IgE) responses, and their widespread use in infant immunisation has been implicated in the recent rise in allergic diseases in the Western world. Although alum enhances antibody responses to vaccine components, it is not particularly effective at inducing cellular immunity, considered critical in control of intracellular pathogens such as HIV, Hepatitis C, Mycobacteria tuberculosis, Plasmodium falciparum or against tumours and is not a suitable adjuvant for mucosal (oral/nasal) immunisation.

While adjuvants such as Monophosphoryl lipid A (MPL), Quil-A, saponin and their derivatives (eg. QS7 and QS21) have been shown to elicit cellular immunity to vaccine components, their manufacture requires extensive extraction and purification procedures to remove toxicity and retain adjuvanticity, which reduce vaccine cost effectiveness. Moreover, the adjuvant activity of MPL formulations administered by mucosal routes is currently unproven in man.

While currently available vaccines primarily target the systemic immune system, most pathogens associated with global morbidity and mortality are transmitted across the mucosal surfaces of the body, initiating either localized infection (eg. rotavirus, the parainfluenza viruses and respiratory syncytial virus) or are disseminated from the mucosa to systemic tissues (eg. HIV, measles and Mycobacteria tuberculosis). Vaccines that can prevent pathogen dissemination from the initial site(s) of infection are likely to be more successful than those that target the blood or disease stage tissue or organs. However, the development of vaccines directed to the mucosal surfaces of the body has been stymied by the lack of adjuvants licensed for use at mucosal surfaces. Control of childhood infection with rotavirus, the parainfluenza viruses and respiratory synyctial virus, would significantly benefit by combining vaccine components with mucosal adjuvants which can be safely administered to infants below six months of age, without the concerns of allergic disease associated with the currently licensed aluminium salt based adjuvants.

The bacterial toxins, cholera toxin (CT) from Vibrio Cholerae and heat labile toxin (LT) from *E.coli* are powerful adjuvants for mucosal delivery in mice, though lower efficacy is reported in man. Concerns with their enterotoxicity preclude their use in man. Moreover a recent study had shown that CT can redirect vaccine proteins into olfactory tissues and may result in targeting of vaccine components to neuronal tissues (van Ginkel et al 2000). Thus, considerable effort has been directed towards altering the toxicity of CT and LT (Rappuoli et al 1999). Several groups have developed non toxic mutants of CT or LT, most of which have mutations in the CTA1-subunit that result in complete or partial disruption of the enzymatic activity associated with toxicity (reviewed Rappuoli et al 1999). However, all of these mutant holotoxins retain their promiscuous binding to the GM1-ganglioside receptor, leaving a potential ability to bind to all nucleated cells and so gain access to unwanted tissues such as the central nervous system (van Ginkel, et al 2000).

There thus remains a need for new effective systemic and mucosal adjuvants, suitable for human, veterinary, livestock and fisheries use which overcome the disadvantages of currently described compounds or substances with reported adjuvant activity.

There is also a need to provide greater protection against infectious disease for individuals with impaired immune systems (ie the young and the elderly). This is particularly relevant in the developing world, where reduced nutritional status is associated with significantly reduced antibody transfer from mother to child and in the elderly where there is a significant decline in immunity.

Infection in the neonatal, and perinatal period is primarily controlled via antibody acquired from the mother. IgG is transferred across the placenta (Lynden 2001 and Glezen 1999) and IgA from the mothers milk (Nagao 2001). This transfer of maternal antibody to foetus/infant is believed to play an important role in the protection of newborns against both bacterial and virus infections (Nagao 2001, Parissi-Crivelli 2000, Glezen 1999). Boosting the pregnant mother's antibody levels to antigens such as tetanus toxoid and influenza haemagglutinin (HA) has been shown to increase the protection of the foetus without harmful side effects to either mother or child (Glezen 1999). The ability to safely boost maternal antibodies in an antigen-independent manner, through materials, which can be used as a stand-alone immune potentiator, would be highly beneficial.

Elderly individuals demonstrate a reduced capacity to be successfully vaccinated (Ben-Yedidia et al 1998) with defects in their ability to mount protective immune responses (Fujihashi et al 2000). This is particularly important in stimulating protective immunity by annual vaccination against the new stains of influenza, which circulate and are a major cause of morbidity and mortality in the elderly. Both B and T cell responses are significantly decreased within the mucosal and systemic compartment with ageing (Fujihashi et al 2000). An aged related increase in IL-10 production (which can suppress DC maturation) and a decline in IL-12 production and dendritic cell antigen presentation, in the elderly, suggest functional defects in antigen presentation and T helper function (Spencer et al 1996, Tortorella et al 2002). Therefore, DC maturation factors, provided by adjuvants could provide the threshold level of co-stimulation required to initiate priming for vaccine induced T and B cell responses. Presently, alum is universally used an adjuvant, although its adjuvant properties are only minimally effective in the elderly when compared to the responses elicited by the same vaccine preparations used in young recipients (Davenport et al 1968). While several new adjuvants have been evaluated, studies demonstrate that (with the possible exception of MF59) these adjuvants have been ineffective in the elderly (Danenberg et al 1997).

Thus the development of a safe, non-reactogenic adjuvant which can enhance the immunogenicity of vaccines (eg against influenza virus, respiratory syncytial virus and the parainfluenza viruses) in the elderly is a high priority.

In accordance with the present invention, a composition for administration to a human or animal subject comprises spores of *Bacillus subtilis* (*B. subtilis*) in amount effective to stimulate or enhance immune responsiveness in the subject. Compositions according to the invention are capable of achieving either (a) an adjuvant effect, or (b) an immunomodulatory effect, or (c) an immune potentiation effect, or (d) a Dendritic cell maturation effect, or (e) any combination of two or more of effects (a) to (d). The ability of *B. subtilis* of spores to produce these varied effects is comprehensively demonstrated in the following description, especially in the section headed EXAMPLES.

The terms used above have connotations well-known to those skilled in the art. Thus, an adjuvant is a substance that enhances the immune response to an antigen with which it is administered. An immune modulator is a substance which changes the type (skews) the immune response without necessarily increasing it. An immune potentiator is a substance which increases or generates greater longevity of a pre-existing immune response. A dendritic cell maturator increases the ability of these cells to activate T cells.

Preferably the spores used for the purposes of the present invention are germination-deficient spores. These may be formulated either with antigenic materials, conveniently by simple admixture, or without such components, in which case the spores function alone as a cell maturator or activator of antigen-presenting cells, or as a non-specific booster of innate and humoral immunity, or as a booster of T independent and T dependent humoral immune responses. One such use of spores alone is for the preparation of a stand-alone vaccine either to boost waning immunity from a previous vaccination or as an immune booster for the elderly or for travellers; such a composition will consist essentially of spores and a suitable pharmaceutically and physiologically acceptable carrier or diluent.

Spores of *B. subtilis* may also be used in vitro to mature Dendritic cells and other antigen-presenting cells prior to administration of these e.g by returning isolated and treated cells to the patient. .

*Bacillus subtilis:*

*B. subtilis* is a non-pathogenic Gram positive soil organism, which under conditions of nutrient deprivation forms spores, which are heat stable and resistant to UV radiation. For the last 30 years a commercial preparation of Bacillus spores (Enterogermina, Sanofi Winthrop, Milan Italy) has been licensed as a probiotic and reported to prevent or treat bacterial diarrhoea, though little was understood about the therapeutic effect. A few clinical reports have mentioned effects on the immune system associated with oral administration of the Enterogermina Bacillus spores obtained from the Sanofi Winthrop Company (Fiorini et al 1985, Cipriandi et al 1986a, Caruso et al 1993). These reports suggested that peripheral blood T-lymphocytes were activated following oral administration of Bacillus spores licensed as Enterogermina. In vitro studies have demonstrated that only the vegetative form and not the sporogenic form of the Enterogermina Bacillus obtained from the Sanofi-Winthrop Company (Cipriandi et al 1986b) induce lymphocyte activation. It was subsequently demonstrated that the spores present within the Enterogermina product germinate and colonize the intestinal tract (Mazza P, 1994). Current knowledge would thus ascribe the probiotic activity observed by Fiorini et al 1985, Cipriandi et al 1986b and Caruso et al 1993 with the vegetative cell, following germination of the orally delivered Enterogermina spore product.

Recently, a group in the UK reported that the probiotic preparations labelled as "*B. subtilis*", currently available in Europe as Enterogermina (Sanofi-Winthrop) or Domuvar (Consorzio Farmaceutico e Biotechnologico Bioprogress a.r.i., Anagi-FR, Italy) and in S.E. Asia as Bactisubtil (Pharmaceutical Factory 24, Ho Chi Minh City, Vietnam), are mislabelled and in fact contain spores from Bacillus species which are taxonomically and phylogenetically unrelated to *B. subtilis* (Green et al 1999, Hoa et al 2000). The distinct taxonomic status of the Bacillus spores marketed as Enterogermina from *B. subtilis* has been confirmed (Senesi et al 2001). These authors also provide evidence that the Bacillus spores contained in commercial preparations of Enterogermina analysed from 1975 to the current date have remained genetically stable and are unequivocally members of the *Bacillus alcalophilus* subgroup, species *B. clausii*.

There is a report suggesting that bacterial cells of *B. subtilis* and also an enzyme (Subtilisin) derived from the bacterial cell of *B. subtilis* (of unknown taxonomic status) augment cutaneous anaphylaxis, a serious immunopathologic reaction (Malkiel et al 1971). However, the spores were reported to be ineffective (Malkiel et al 1971). A protein component termed Protodyne reported as common to several genera of Gram-negative and Gram-positive bacteria (including *B. subtilis*) derived from the bacterial protoplasm was described to exert an immunostimulatory activity (Houba et al 1992). Contemporary knowledge may ascribe Protodyne as peptidoglycan-techoic acid, derived from the cell wall of many bacterial cells (including *B. subtilis* vegetative cells) which is weakly pyrogenic and mitogenic (Hinmanen et al 1993).

In summary, there are conflicting probiotic and immunopathologic reports attributed to the vegetative cells of *B. subtilis* (and other genera of Bacilli) without documentation of any adjuvanticity, B cell or DC immunopotentiatory or immunomodulatory or DC maturation activity associated with the sporegenic form.

The invention uses spores of *B. subtilis* subspecies subtilis (also known as Ehrenberg 1835 or Cohn 1872); defined as all Bacillus strains which contain a 16SrRNA [small subunit ribosomal RNA] 99% similar at the genetic level to the *B. subtilis* strain 168 [ATCC number 23857] (Maidak et al, 2000), where the biochemical, metabolic and morphological properties of currently known Bacillus strains are defined by Bergey's Manual of Systematic Bacteriology, section 13, pp 1104-1139. Examples of *B. subtilis* strains with 99% or higher 16S rRNA genetic similarity includes ATCC numbers; 9799, 35148, 15563, 33234, 55567.

The invention uses spores from *B. subtilis* as an adjuvant by simply admixture with a candidate vaccine to boost the immune response to the vaccine components Attributes of *B. Subtilis* Spores:

The spores are extremely cheap to produce, do not require purification procedures, are heat and UV stable, and therefore do not require cold chain storage. They are suitable for incorporation into pharmaceutical compositions for administration as suspensions or from a lyophilised form, thus affording indefinite storage, and are suitable for systemic or mucosal delivery e.g by intravenous, intradermal, intramuscular, subcutaneous, transdermal or intraperitoneal administration or by oral, nasal, respiratory, pulmonary topical, gill delivery, intrathecal, buccal (sublingual), rectal or vaginal delivery. The dose at which the substance of the invention is administered to a patient or to an animal will depend upon a variety of factors such as the age, weight and general condition of the patient, the condition that is being treated and the route by which the substance is being administered. A suitable dose may however be $10^5$ to $10^{11}$ spores per dose. If doses in this range are not sufficient, the dose may be increased. Those skilled in the art will recognise the appropriate dosage level to test, from research reported herein. Without intending any limitation as to course of treatment, the adjuvant, immunemodulator, immune potentiator or dendritic cell-maturating agent/innate stimulator could be administered on a number of occasions.

*B. subtilis* is classified by the term, GRAS (generally regarded as safe) organism, thus germination competent spores can be used. For certain applications it will be desirable to use germination deficient spores, which can also be administered to individuals with immunocompromised immune systems, where the adjuvant activity of the spore may safely augment the immunogenicity of a vaccine. This has particular application to childhood vaccination, particularly in the first year of life and also to individuals with acute/chronic acquired immunodeficiency, through infection with HIV, measles, or *Mycobacteria tuberculosis*. The use of germination deficient spores provides additional benefit, in veterinary and commercial livestock, poultry or fish vaccine applications, where there are concerns of antibiotic resistance transfer to man associated with live bacterial vectors or probiotics used in oral bacteriotherapy.

Germination deficient spores can be generated by heat inactivation or by inactivation of *B. subtilis* genes, examples of which include the following list of genes (followed by their accession number): gerAA P07868, gerAB P07869, gerAC P07870, gerBA P39569, gerBB P39570, gerBC P39571, gerD 555 P16450, gerE 222 P11470, gerKA P49939, gerKB P49940, gerKC P49941, gerM P39072.

The present invention is to be distinguished from the use of *B. subtilis* spores as a vaccine vector in which antigenic sequences are cloned and expressed i.e as an epitope presentation system.

BRIEF DESCRIPTION OF THE DRAWING FIGURES

FIG. 1: Spores from *B. subtilis* provide a maturation stimulus for immature bone-marrow derived dendritic cells.

Germination-inactivated spores from *B. subtilis* strain 168 were cultured 12 hours in vitro with day five BMDC at a spore to BMDC ratio of 0, 0.1, 1 and 10:1. Cultures were washed and stained with fluorochrome-conjugated monoclonal antibodies to MHC class II and the co-stimulatory molecules CD86 and CD40 or isotype-matched antibody controls Stained BMDC were analysed by flow cytometry using a Cytomation (MoFlo cell sorter). Data profiles were obtained after analysis of 20,000 events. Staining with cell surface specific monoclonal antibodies is depicted by the grey filled peaks and by isotope matched control monoclonal antibodies by the black empty peaks.

Figure 2:
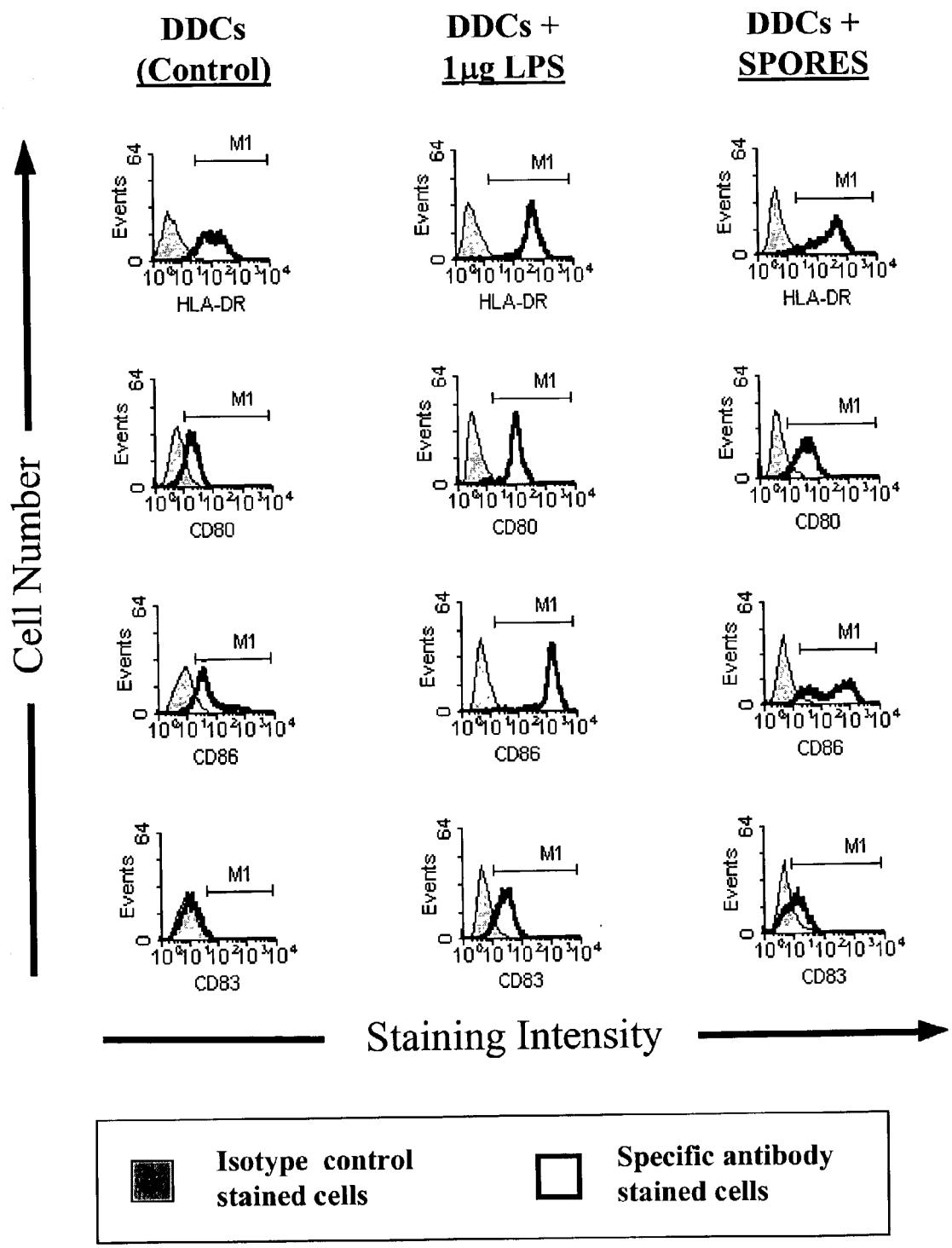

FIG. 2: Spores from *B. subtilis* provide a maturation stimulus for immature human monocyte derived dermal dendritic cells.

Germination-inactivated spores from *B. sublilis* strain 168 were cultured 48 hours in vitro with day 10 human monocyte derived dermal dendritic cells (DDC) at a spore to DDC ratio of 0 and 10:1 and compared to lipopolysaccaride (LPS) stimulated cultures. Cultures were washed and stained with fluorochrome-conjugated monoclonal antibodies to HLA-DR (human MHC class II) and the co-stimulatory molecules CD80 and CD86 or isotype-matched antibody controls. Stained DDC were analyzed by flow cytometry using a Cytomation (MoFlo cell sorter). Data profiles were obtained after analysis of 20,000 events. Staining with cell surface specific monoclonal antibodies is depicted by the black open peaks and the isotope matched control monoclonal antibodies by the grey filled peaks.

Figure 3:
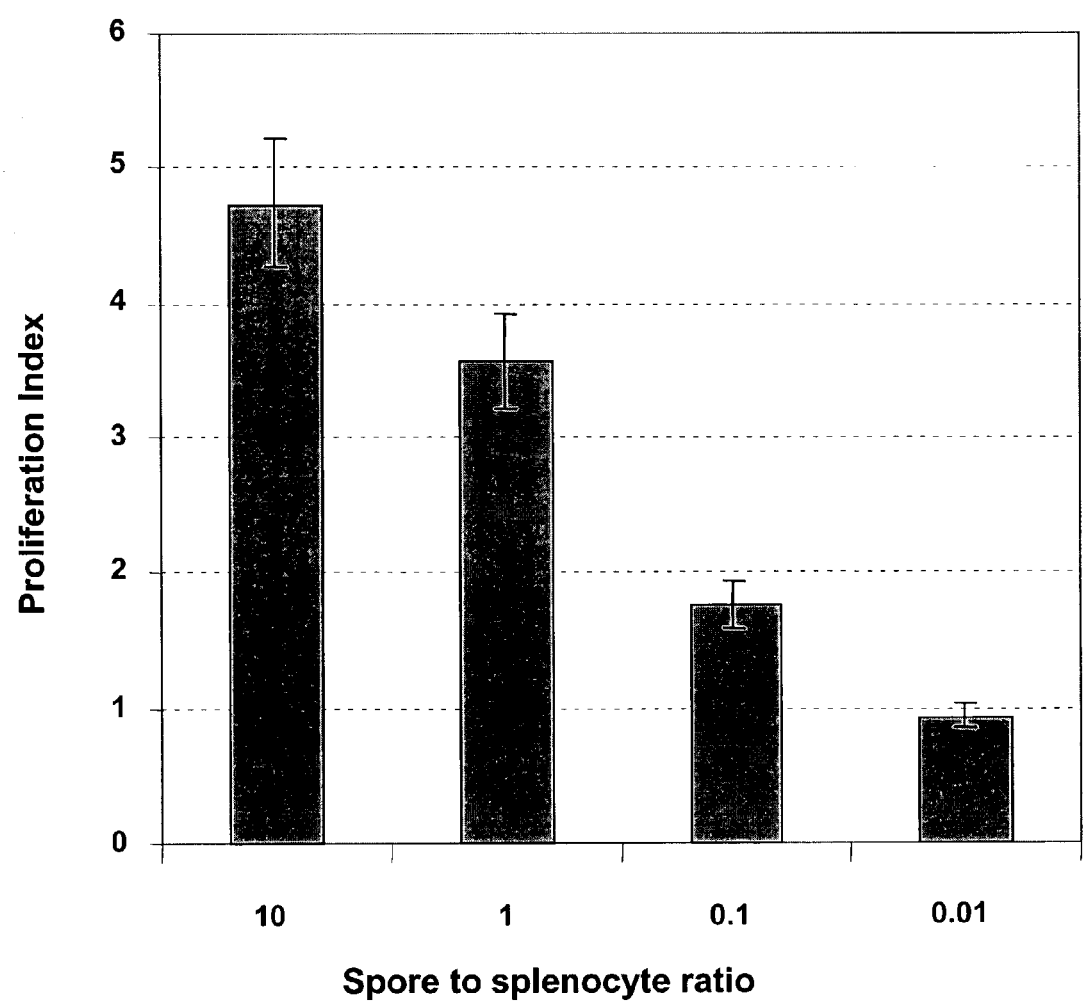

FIG. 3: Spores from *B. subtilis* induce a dose dependant proliferation of naive splenocytes.

Lymphoproliferation of unfractionated splenocytes derived from naive BALB/c mice was evaluated in vitro following stimulation with germination inactivated spores of *B. subtilis* strain 168 at a spore to splenocyte ratio of 10, 1, 0.1 and 0.01:1. On day 3, cultures were incubated with $^3$[H]-thymidine and incorporation quantitated after 12 hrs. Data are expressed as a proliferation index determined from the mean counts (cpm/min) of each stimulated culture divided by the mean counts from control cultures in the presence of medium only. The results represent triplicate cultures from 4 individual mice. The error bars represent the standard deviation from the mean.

Figure 4A:
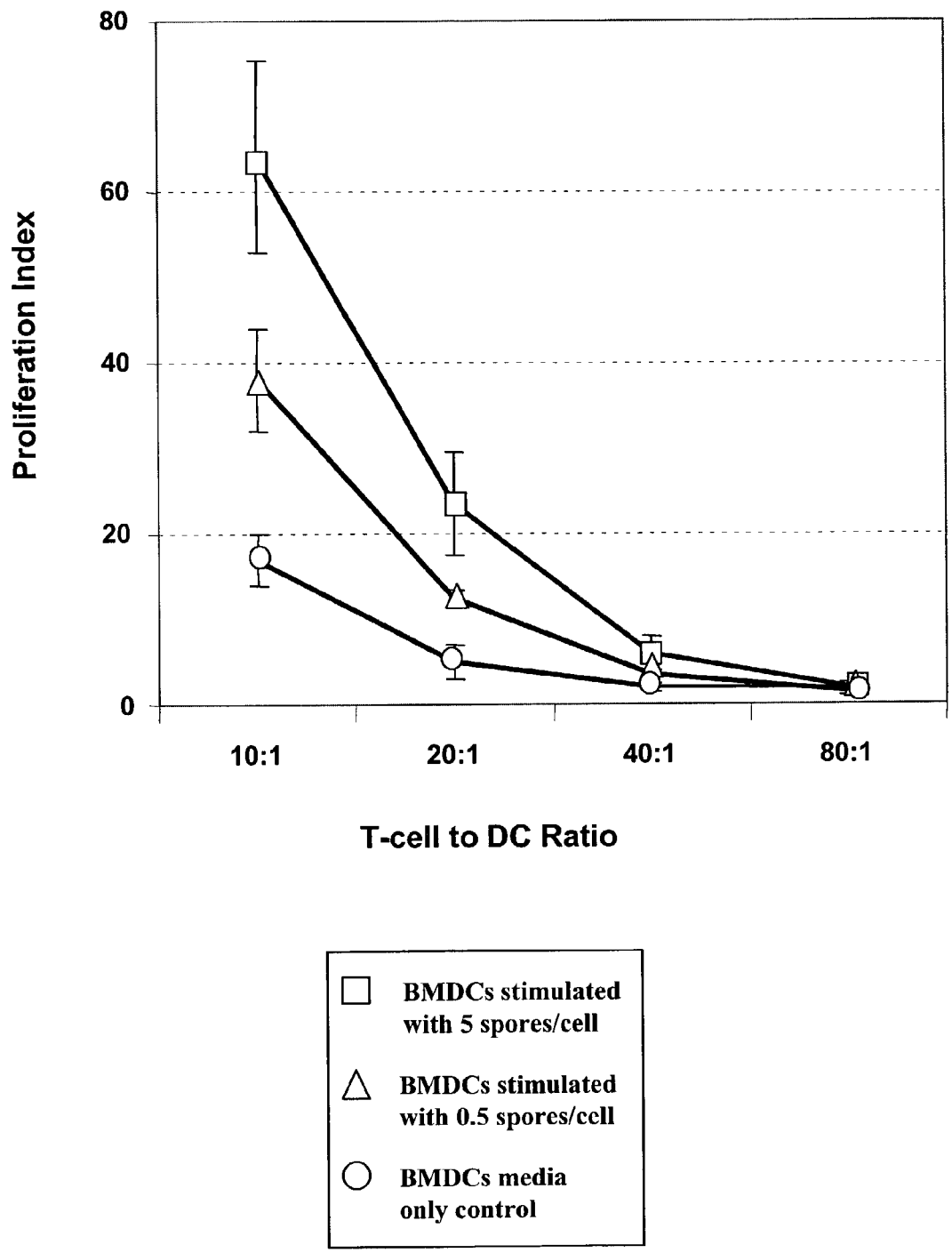

FIG. 4a: BMDC pulsed with spores from *B. subtilis* induce dose dependant proliferation of naive T-cells.

Immature BMDC were pulsed with either germination inactivated spores of *B. subtilis* at a ratio of 5 spores per cell (squares) or 0.5 spores per cell (triangles) or left unpulsed (circles). The BMDC's were then washed and cultured with splenic T-cells for 4 days at ratio's 10 T-cells per DC to 80 T-cells per DC. T cell proliferation was measured by $^3$[H]-thymidine incorporation and are expressed as a proliferation index. The data represent quadruplicate cultures from purified T-cells derived from the spleens of 5 pooled mice. The error bars represent the standard deviation from the mean.

Figure 4B:
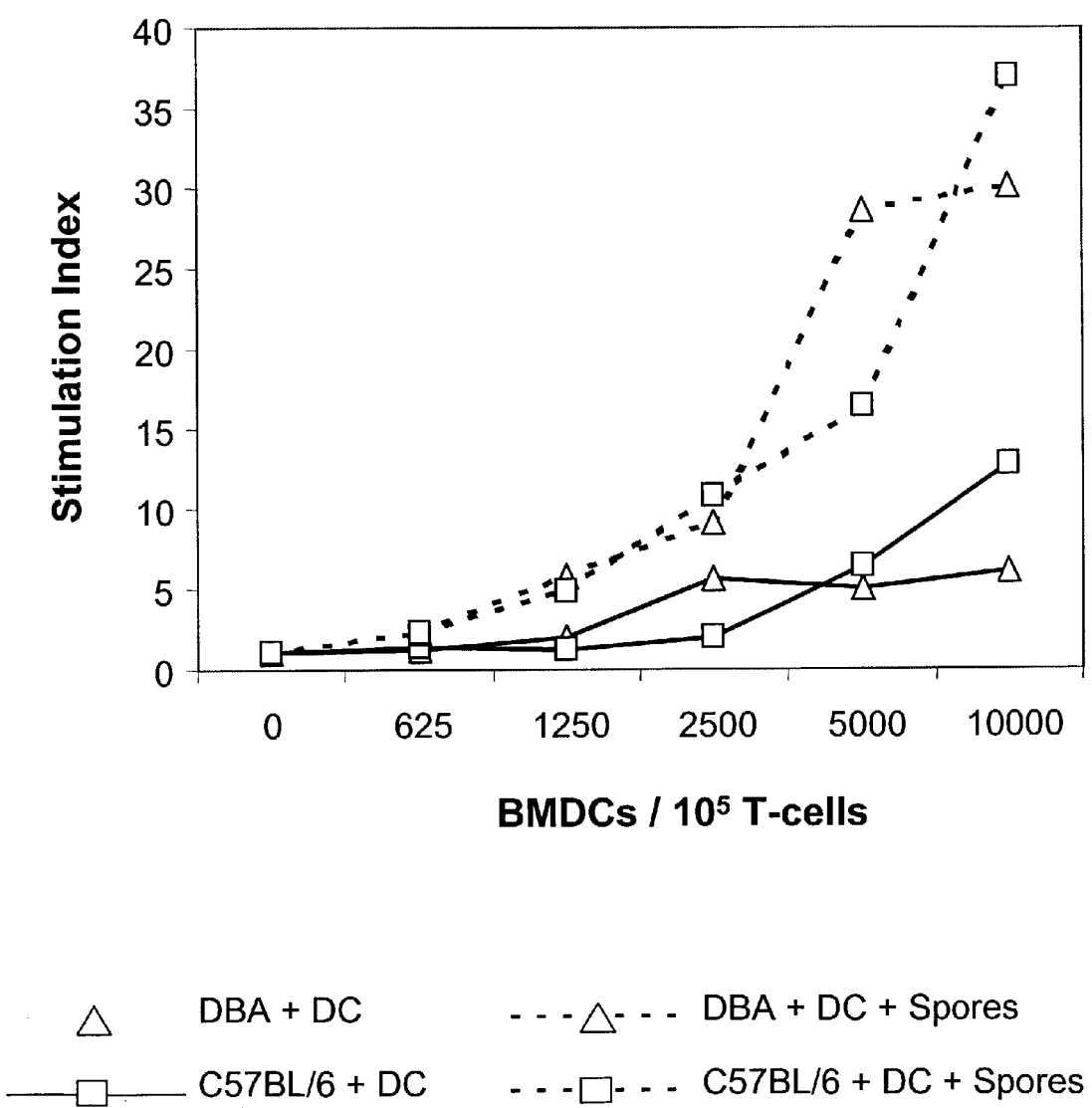

FIG. 4b: BMDC pulsed with spores from *B. subtilis* induce enhanced proliferation of allogeneic T-cells.

Immature BMDC from Balb/c (H-2d) mice were pulsed with either germination inactivated spores of *B. subtilis* at a ratio of 10 spores per cell (dashed lines) or left unpulsed (solid lines). The BMDC's were then washed and cultured with $10^5$ naive splenic T-cells from DBA (H-$2^k$) mice (triangles) or C57BL/6 (h-$2^b$) mice (squares) for 4 days at ratio's of 625 BMDCs per $10^5$ T-cells to 10000 BMDCs per $10^5$ BMDCs. T-cell proliferation was measured by $^3$[H]-thymidine incorporation and are expressed as a proliferation index. The data represent triplicate cultures from purified T-cells.

Figure 4C:
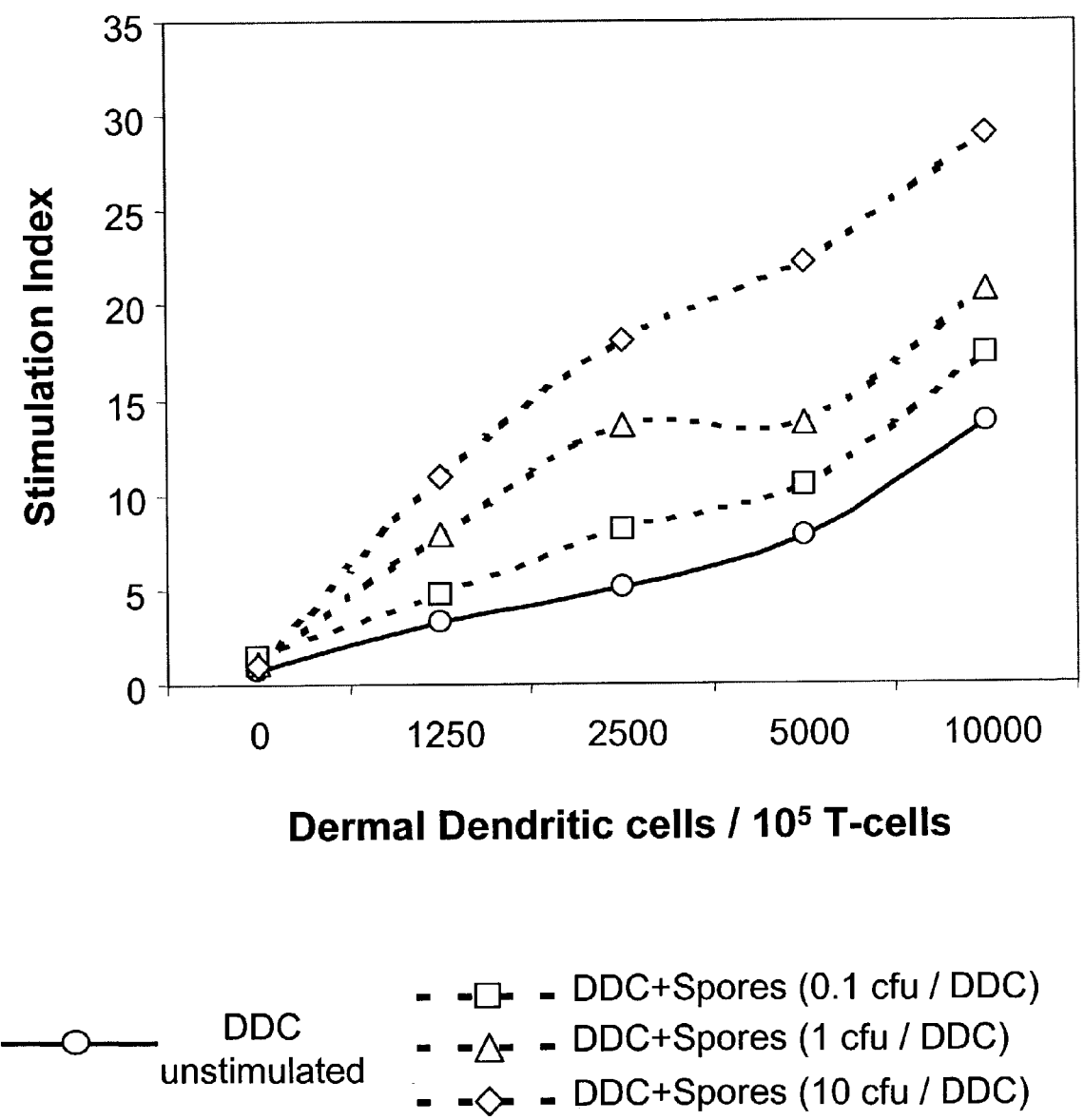

FIG. 4c: Dermal dendritic cells (DDC) pulsed with spores from *B. subtilis* induce enhanced proliferation of allogeneic T-cells.

Immature human monocyte derived DDC's were either pulsed with germination inactivated spores of *B. subtilis* (dashed lines) or left unpulsed (solid lines with circles). The DDCs with pulsed at ratios of either 10 spores per cell (diamonds), 1 spore per cell (triangles) or 0.1 spores per cell (squares). The DDC's were then washed and cultured with $10^5$ naive splenic T-cells from an allogeneic human donor for 5 days at ratio's of 1250 DDCs per $10^5$ T-cells to 10000 DDCs per $10^5$ BMDCs. T-cell proliferation was measured by $^3$[H]-thymidine incorporation and are expressed as a proliferation index. The data represent triplicate cultures from purified T-cells.

Figure 5:
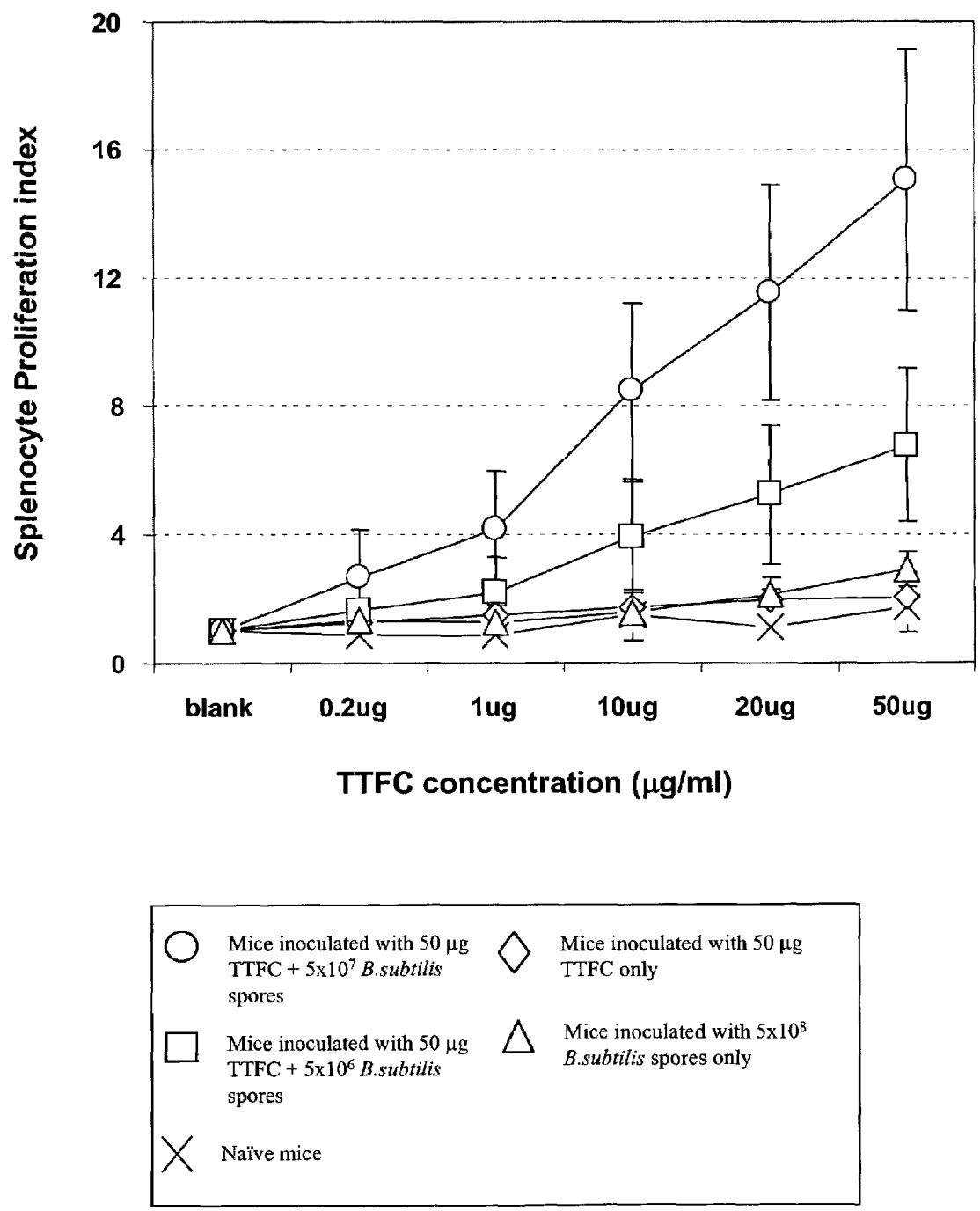

FIG. 5: Spores from *B. subtilis* enhance T-cell proliferative responses to co-inoculated target antigens in mice.

Groups of Balb/c mice were inoculated on days 0, 14 and 28 via the subcutaneous route with either 50 μg of TT in PBS (diamonds), $5\times10^8$ *B. subtilis* spores in PBS (triangles), 50 μg of TT with $5\times10^6$ *B. subtilis* spores in PBS (squares) or 50 μg of TT with $5\times10^7$ *B. subtilis* spores in PBS (circles). On day 42, splenocytes were isolated from each group and lymphoproliferation compared to naive splenocytes (crosses) following 3 day culture in the presence or absence of a range of TT concentrations in vitro. Proliferation is expressed as a proliferation index. The data represent quadruplicate cultures from each of 5 mice in each group. The error bars represent the standard deviation from the mean.

Figure 6:
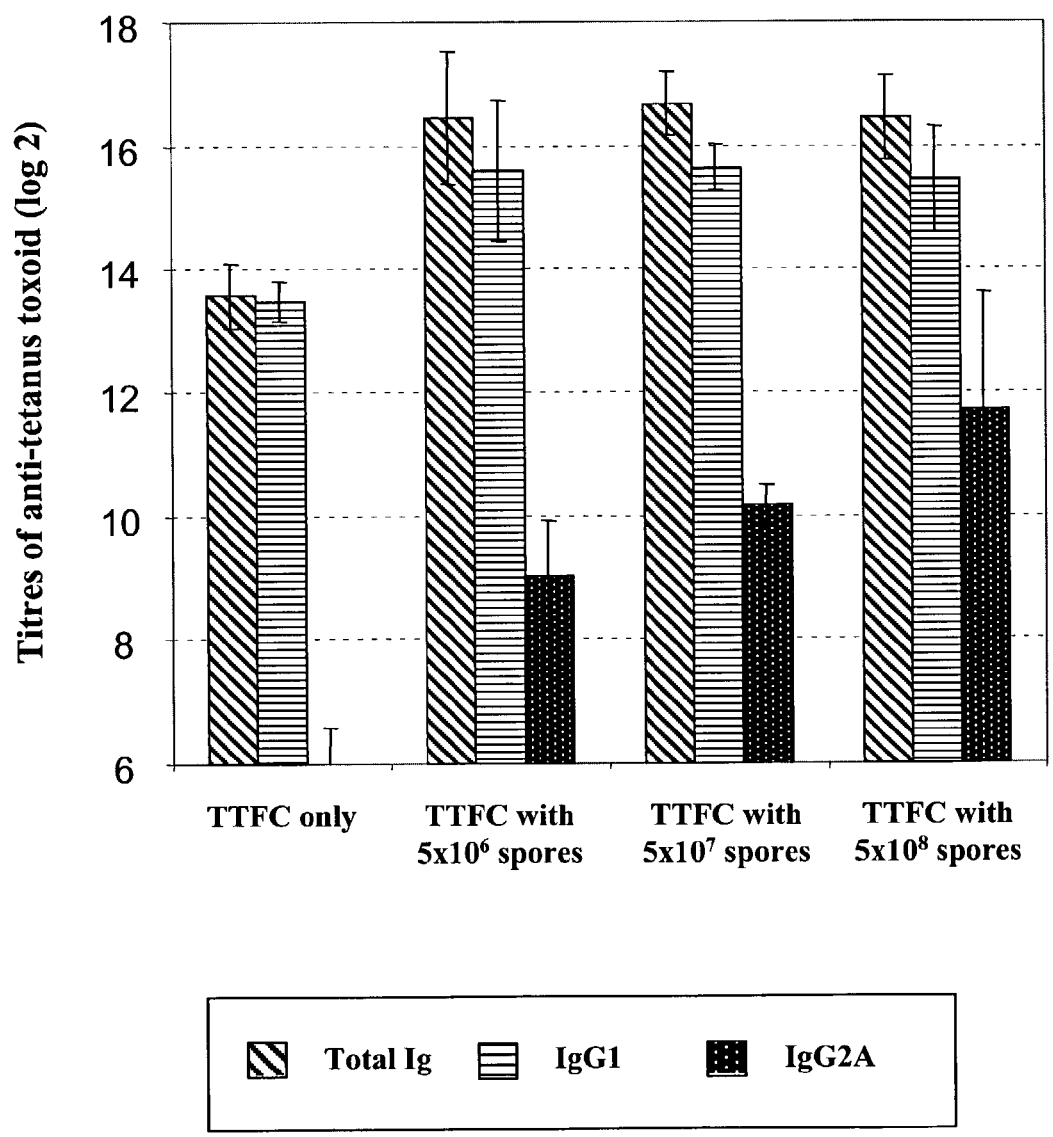

FIG. 6: Spores from *B. subtilis* enhance serum antibody responses to co-inoculated target antigens in mice.

Groups of Balb/c mice were inoculated by the subcutaneous route on day 0 and boosted by the intraperitoneal route on day 14 with either 5μg of TT in PBS, or 5 μg of TT with either $5\times10^6$, $5\times10^7$, or $5\times108$ *B. subtilis* spores in PBS. On day 42 mice were euthanised and serum collected. Total TT-specific serum Ig (open bars with diagonal lines), TT-specific IgG1 (open bars with horizontal lines) and TT-specific IgG2a (black bars with white spots) were determined by TT-specific ELISA. The data represent the mean titre determined from 5 mice per group. The mean cut off point is expressed as the number of halving dilutions required to be significantly above the pre-bleed sera. The error bars represent the standard deviation from the mean.

Figure 7:
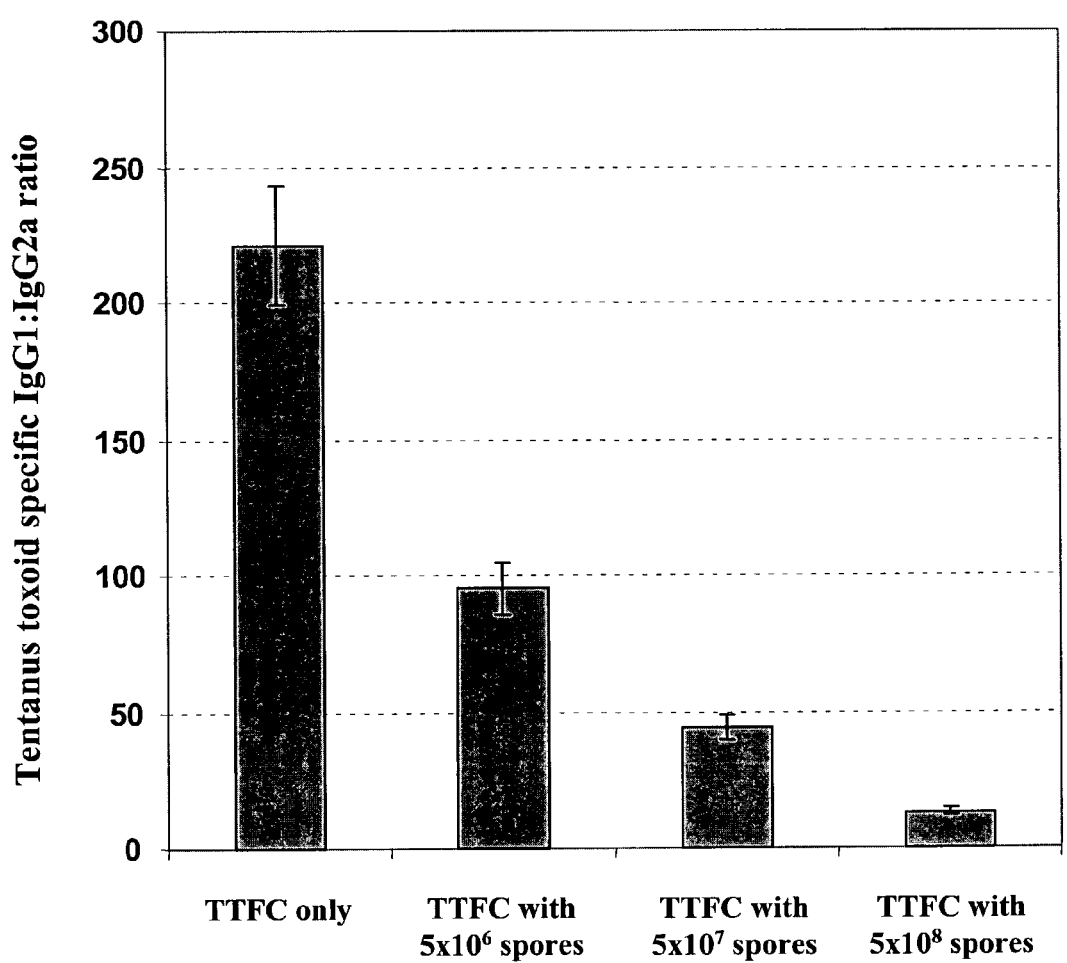

FIG. 7: Spores from *B. subtilis* induce a mixed Th1/Th2 antibody response in a dose dependant manner.

The figure represents the ratio of TT-specific IgG1 titre divided by the TT-specific IgG2a titre, generated by the mice from FIG. 6. The bars represent the mean IgG1:IgG2a ratio of the 5 mice in each group. The error bars represent the standard deviation from the mean.

Figure 8:
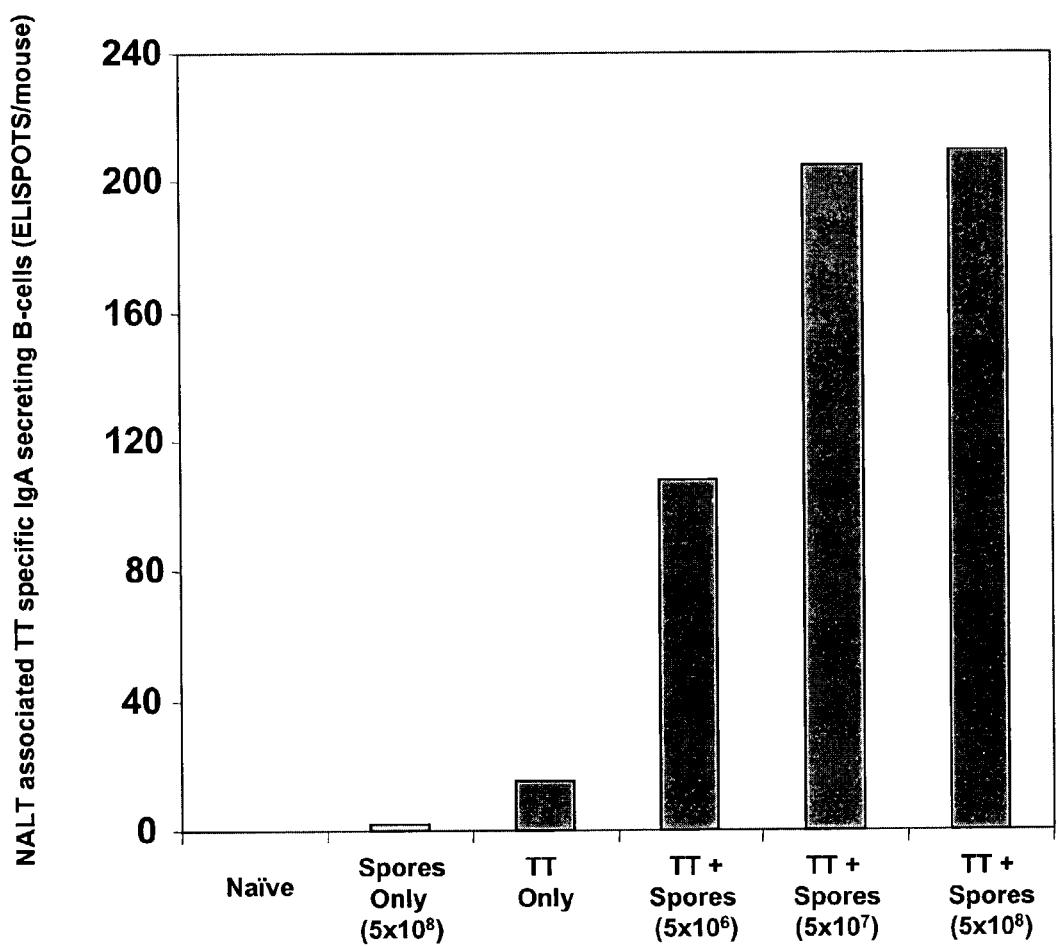

FIG. 8: Spores from *B. subtilis* boost the number of target antigen specific antibody secreting cells at the mucosal surface.

Balb/c mice (5 per group) were inoculated on days 0, 14 and 28 via the intra-nasal (in) route with either: 10 μg TT, $5\times10^8$ *B.subtillis* spores, or 10 μg TT co-administered with either $5\times10^6$, $5\times10^7$ or $5\times10^8$ *B. subtilis* spores. Naïve mice were included as a negative control. On day 42, nasal associated lymphoid tissues (NALT) were removed to enumerate TT-specific IgA antibody secreting B cells by ELISPOT assay. The data represents the mean total number of TT-specific IgA spot forming cells per mouse per group.

Figure 9:
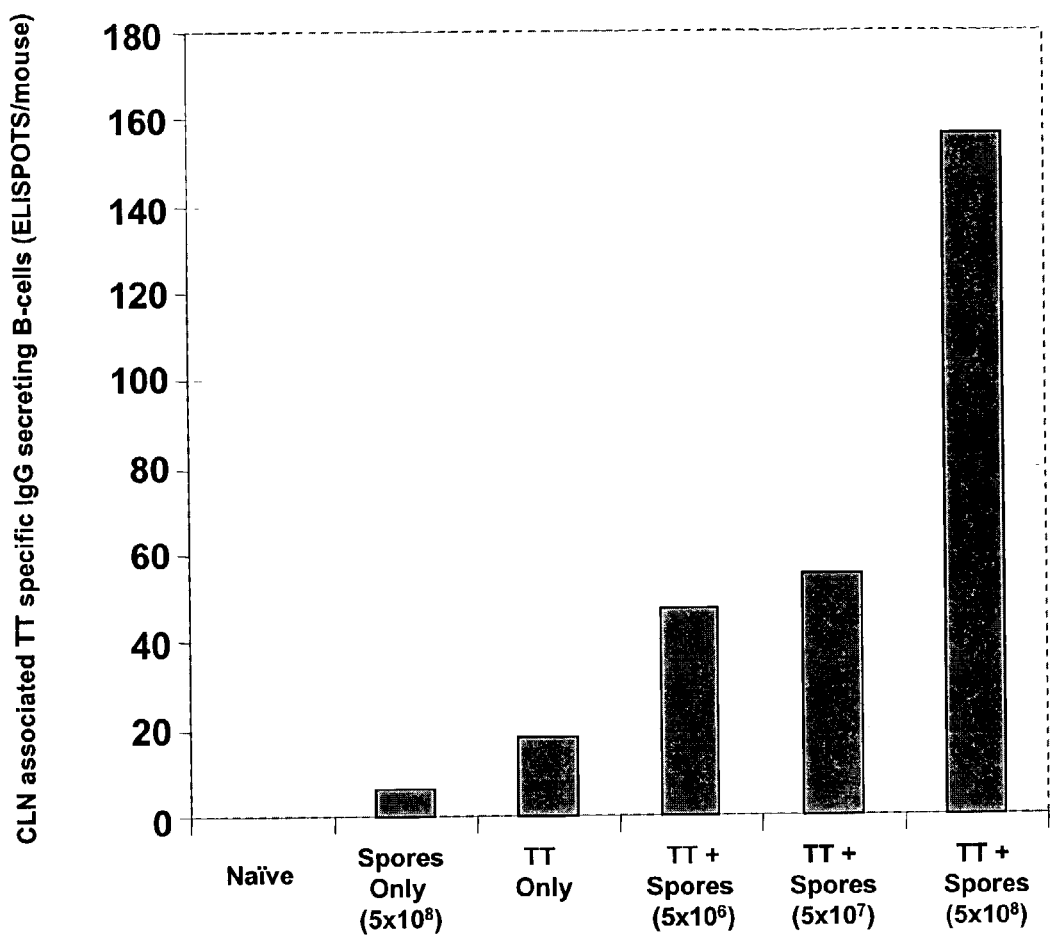

FIG. 9: Spores from *B. subtilis* boost the number of antigen specific antibody secreting B cells in lymph nodes draining the site of vaccine administration.

Lymphocytes isolated from the cervical lymph nodes (CLN) from each of the groups of mice in FIG. 8 were analysed for the number of TT-specific IgG secreting B-cells by ELISPOT assay. The data represent the mean total number of TT-specific IgG spot forming cells per mouse per group.

Figure 10:
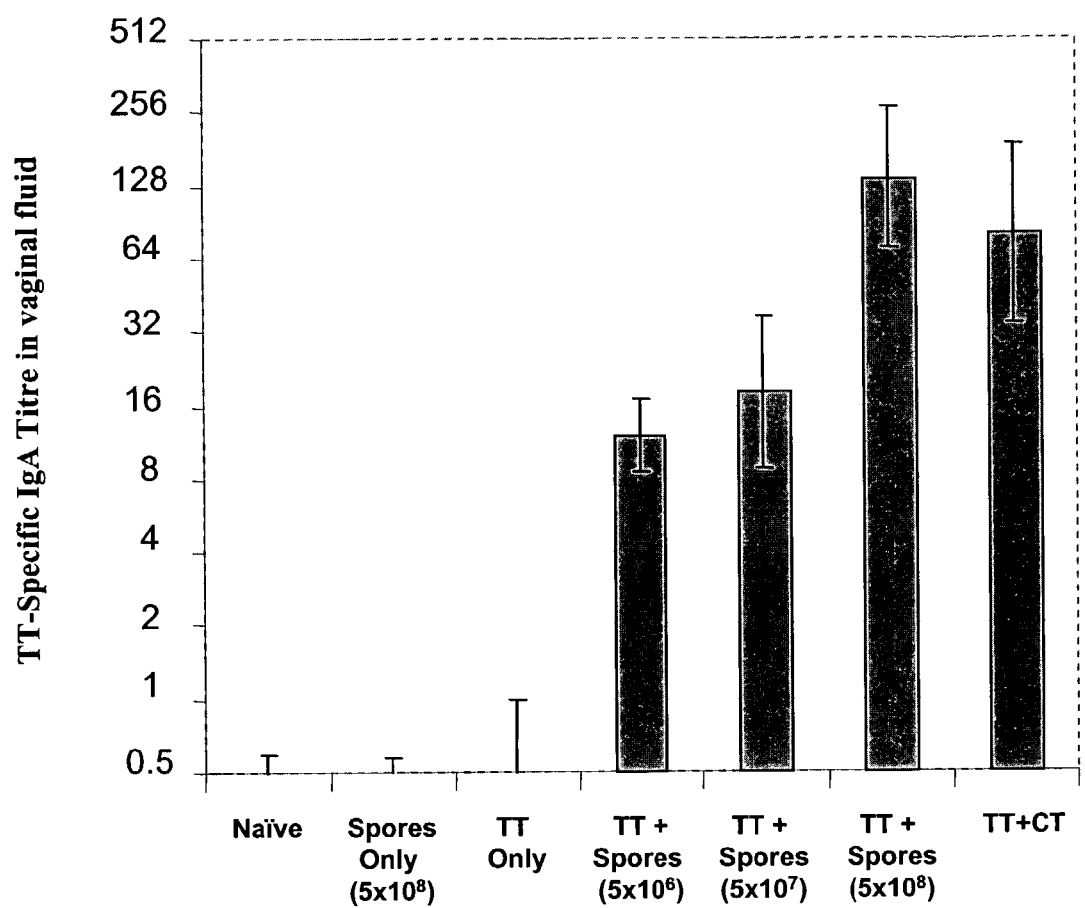

FIG. 10: Spores from *B. subtilis* boost antigen specific secretory IgA antibody at mucosal sites distal from the site of vaccine administration.

Vaginal washings were analysed by TT-specific ELISA assay from each of the groups of mice in FIG. 9 at day 35 post intranasal vaccination. The data represent the mean antibody titre determined from 5 mice per group. The results were expressed as the lowest dilution of serum giving an optical density value (OD) value of 0.1 units above the mean OD value of the cognate pre-immune serum. The error bars represent the standard deviation from the mean.

Figure 11:
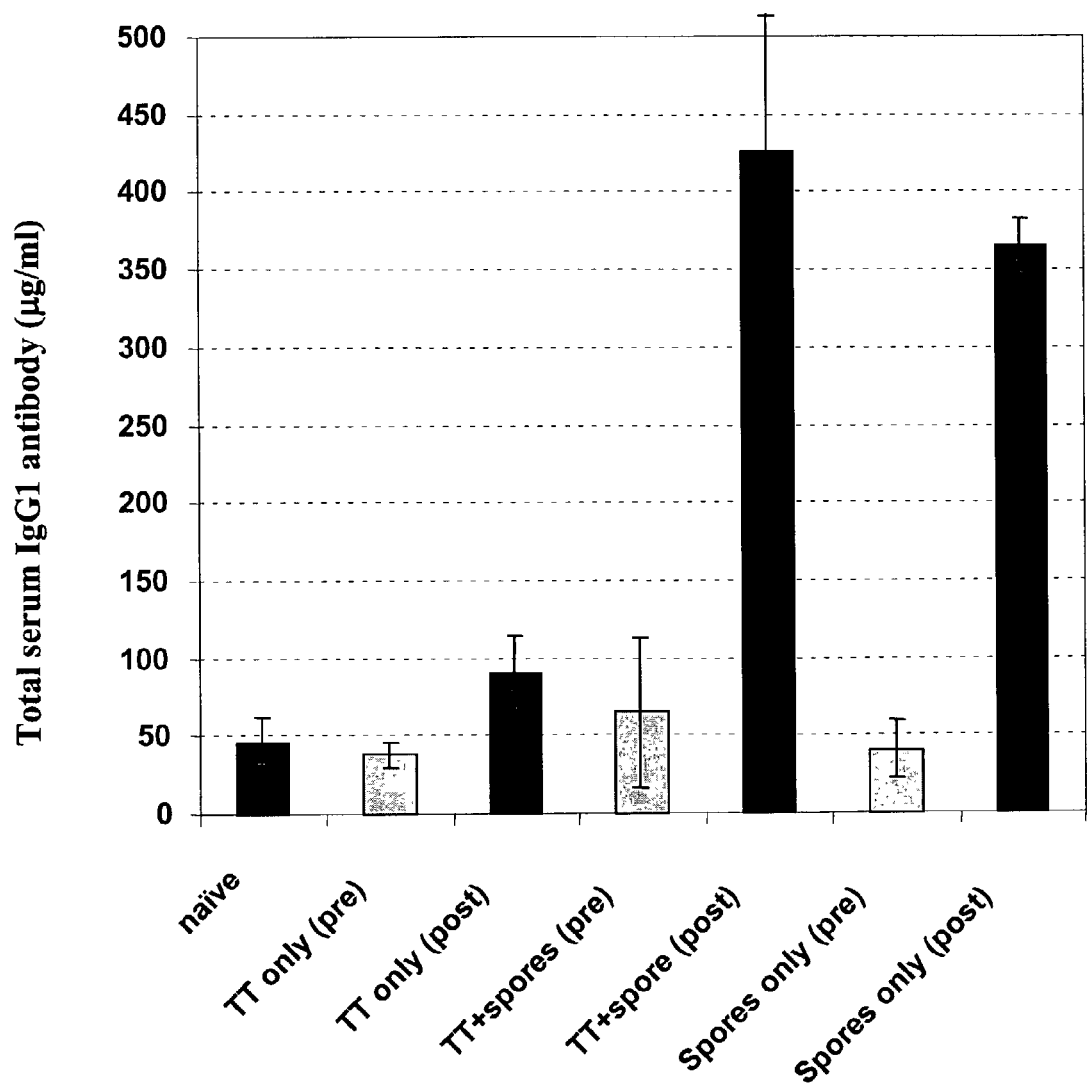

FIG. 11: Spores from *B. subtilis* boost total serum IgG1 antibody responses.

Figure 12:
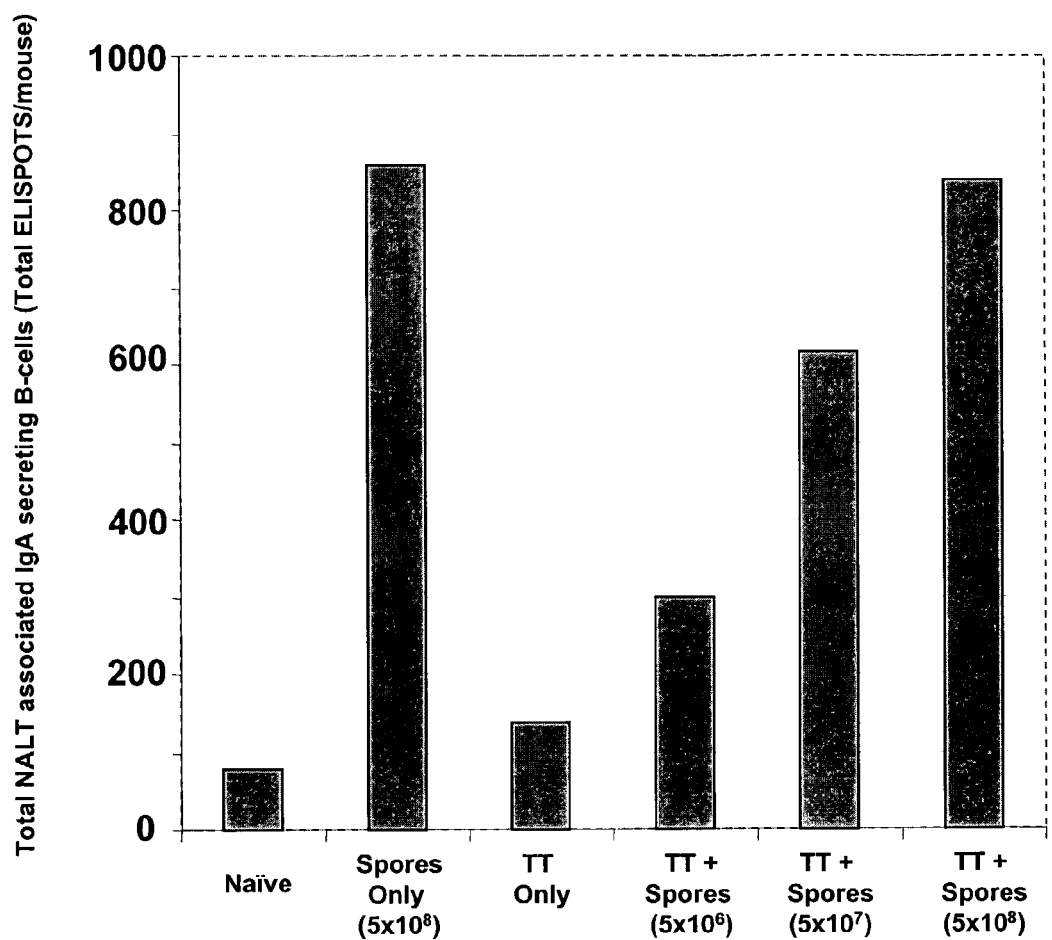

The total levels of serum IgG1 were determined from groups of mice inoculated by the subcutaneous route with either 5 μg of TT in PBS, $5\times10^8$ *B. subtilis* spores in PBS, or 50 μg of TT with $5\times10^6$ *B. subtilis* spores in PBS. Naïve mice were included as vaccination controls. Total serum IgG1 was analysed pre-immunisation (black bars) and following the final immunisation on day 42 (open bars) by single radial immunodiffusion assay. The results are presented as the mean IgG1 concentration (μg/ml) plus the standard error from the mean. N=5 mice per group.

FIG. 12: Spores from *B. subtilis* boost the number of antigen specific antibody secreting B cells at the mucosal surface.

The total numbers of IgA secreting B-cells present in NALT tissues of the mice reported in FIG. 8, was enumerated using a pan anti-IgA ELISPOT assay. The data represents the mean total number of IgA spot forming cells per mouse per group.

Figure 13:
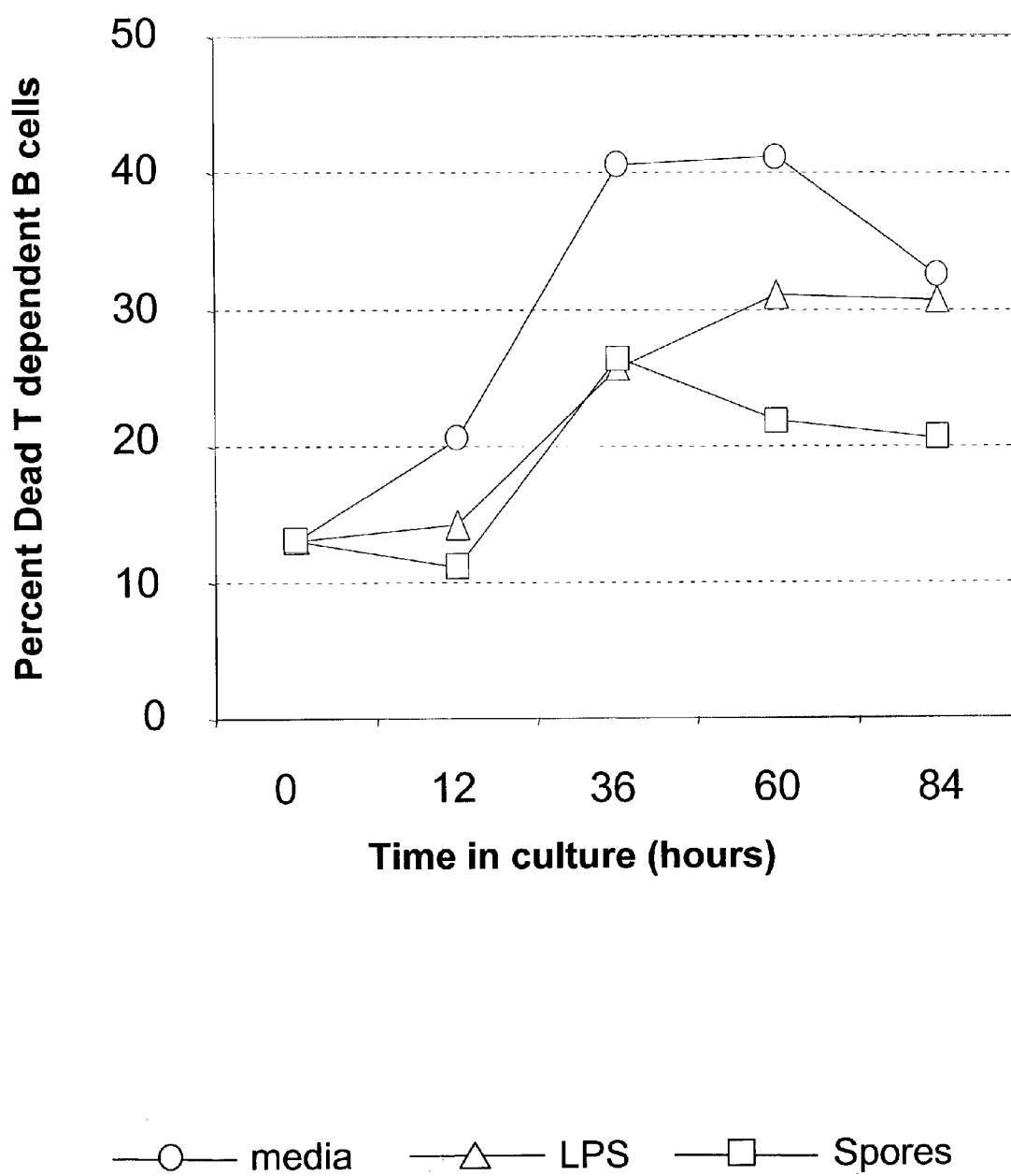

FIG. 13: Spores from *B. subtilis* increase the survival of T-dependant B-cells in vitro.

Splenocytes were cultured with either *B. subtilis* spores ($5 \times 10^7$), LPS (2 µg/ml) or media between 0 and 84 hours. Cells were removed, stained with the monoclonal antibodies, anti-HSA-FITC, anti-B220-CyChrome and anti-CD3, -CD4 and -CD8 conjugated APC. By flow cytometry the gated $B220^{+ve}$, $HSA^{low}$ and $CD3/4/8^{-ve}$ cells were analysed with respect to size (foreword and side scatter). The data represents the proportion of T-dependant B-cells located within the dead cell gate over time in responses to incubation with either *B. subtilis* spores (squares), LPS (triangles) or media alone (circles).

Figure 14:
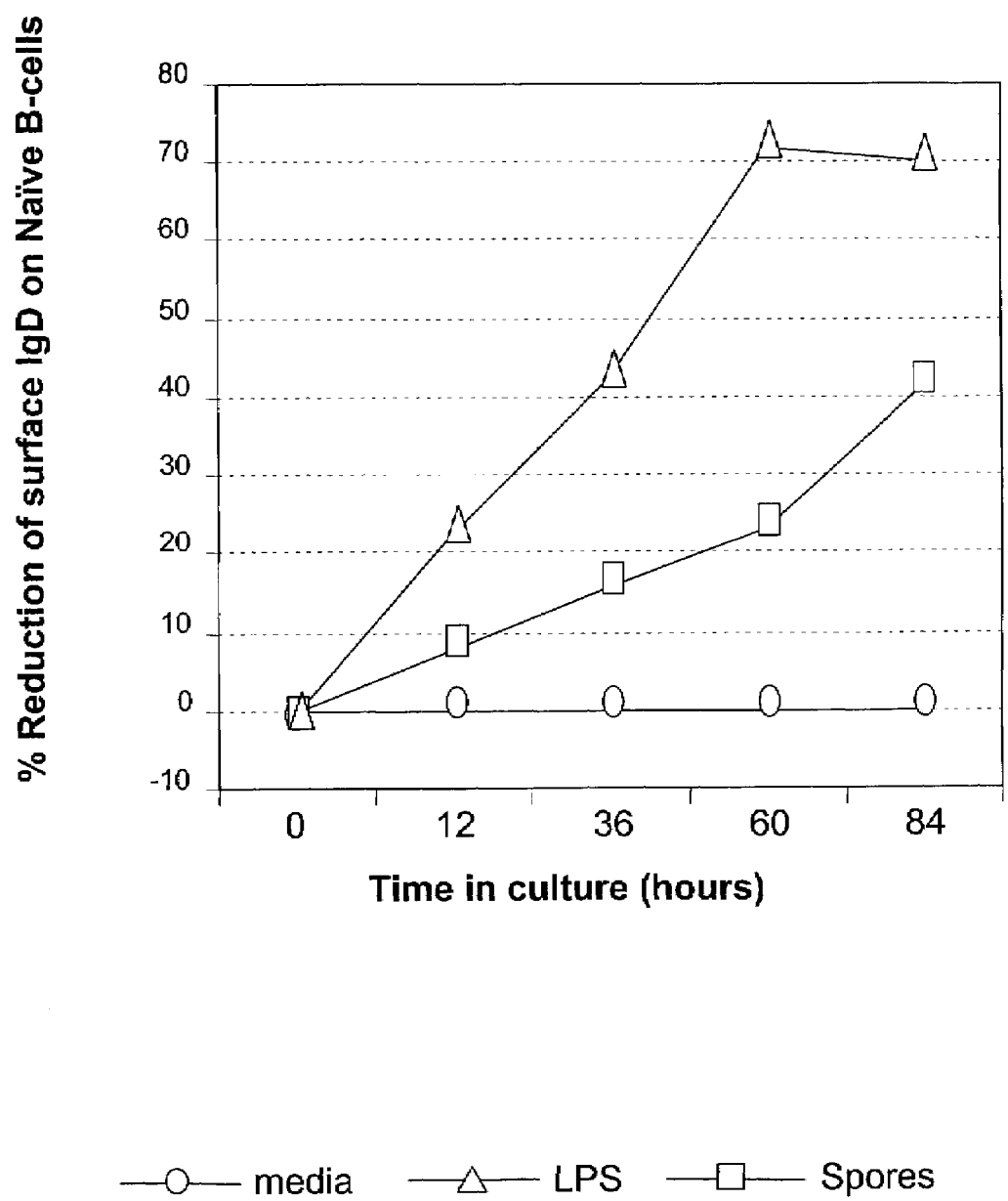

FIG. 14: Spores from *B. subtilis* induce maturation of naive T-dependant B-cells in vitro.

Splenocytes were cultured with either *B. subtilis* spores ($5 \times 10^7$), LPS (2 µg/ml) or media between 0 and 84 hours. Cells were removed, stained with the monoclonal antibodies, anti-HSA-FITC, anti-B220-CyChrome and anti-CD3, -CD4 and -CD8 conjugated APC. By flow cytometry the gated $B220^{+ve}$, $HSA^{low}$ and $CD3/4/8^{-ve}$ cells were analysed with respect to the level of surface IgD. The data represents the reduction in surface IgD expression in responses to incubation with *B. subtilis* spores (squares), LPS (triangles) or media alone (circles).

Figure 15:
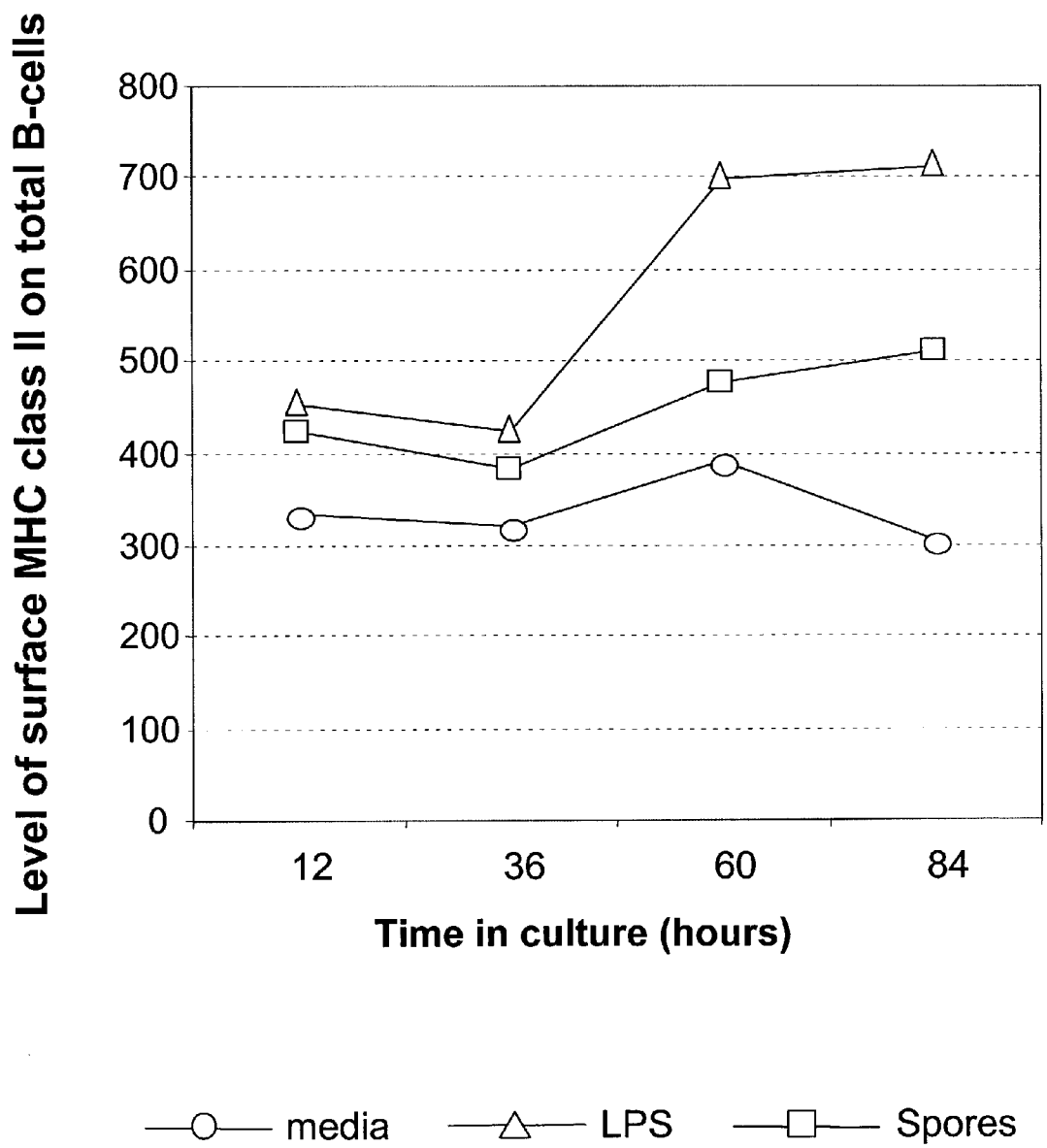

FIG. 15: Spores from *B. subtilis* upregulate surface expression of MHC class H on B-cells in vitro.

Splenocytes were cultured with either *B. subtilis* spores ($5 \times 10^7$), LPS (2 µg/ml) or media between 0 and 84 hours. Cells were removed and stained with the monoclonal antibodies, anti-HSA-FITC, anti-B220-CyChrome and anti-CD3, -CD4 and -CD8 conjugated APC. By flow cytometry the gated $B220^{+ve}$, $HSA^{low}$ and $CD3/4/8^{-ve}$ cells were analysed with respect to expression of surface MHC class II. The data represents the surface expression of MHC class II in responses to *B. subtilis* spores (squares), LPS (triangles) or to just media alone (circles).

Figure 16:
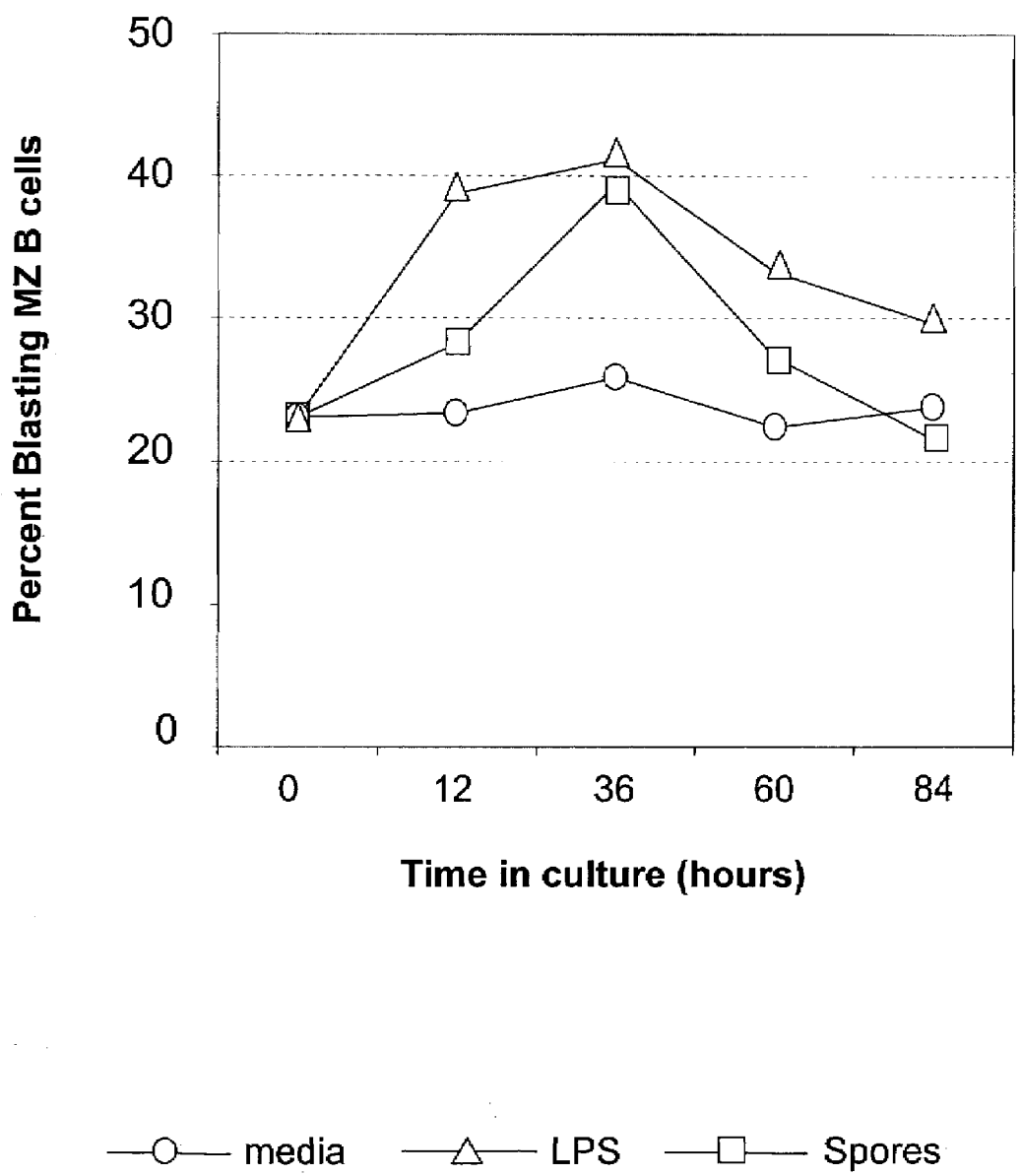

FIG. 16: Spores from *B. subtilis* induce blasting in T-independent (innate) B-cells in vitro.

Splenocytes were cultured with either *B. subtilis* spores ($5 \times 10^7$), LPS (2 µg/ml) or media between 0 and 84 hours. Cells were removed and stained with the monoclonal antibodies, anti-HSA-FITC, anti-B220-CyChrome and anti-CD3, -CD4 and -CD8 conjugated APC. By flow cytometry the gated $B220^{+ve}$, $HSA^{low}$ and $CD3/4/8^{-ve}$ cells were analysed with respect to size (foreword and side scatter). The data represents the proportion of blasted (activated) T-independent Marginal Zone B-cells over time in responses to *B. subtilis* spores (squares), LPS (triangles) or media alone (circles).

Figure 17:
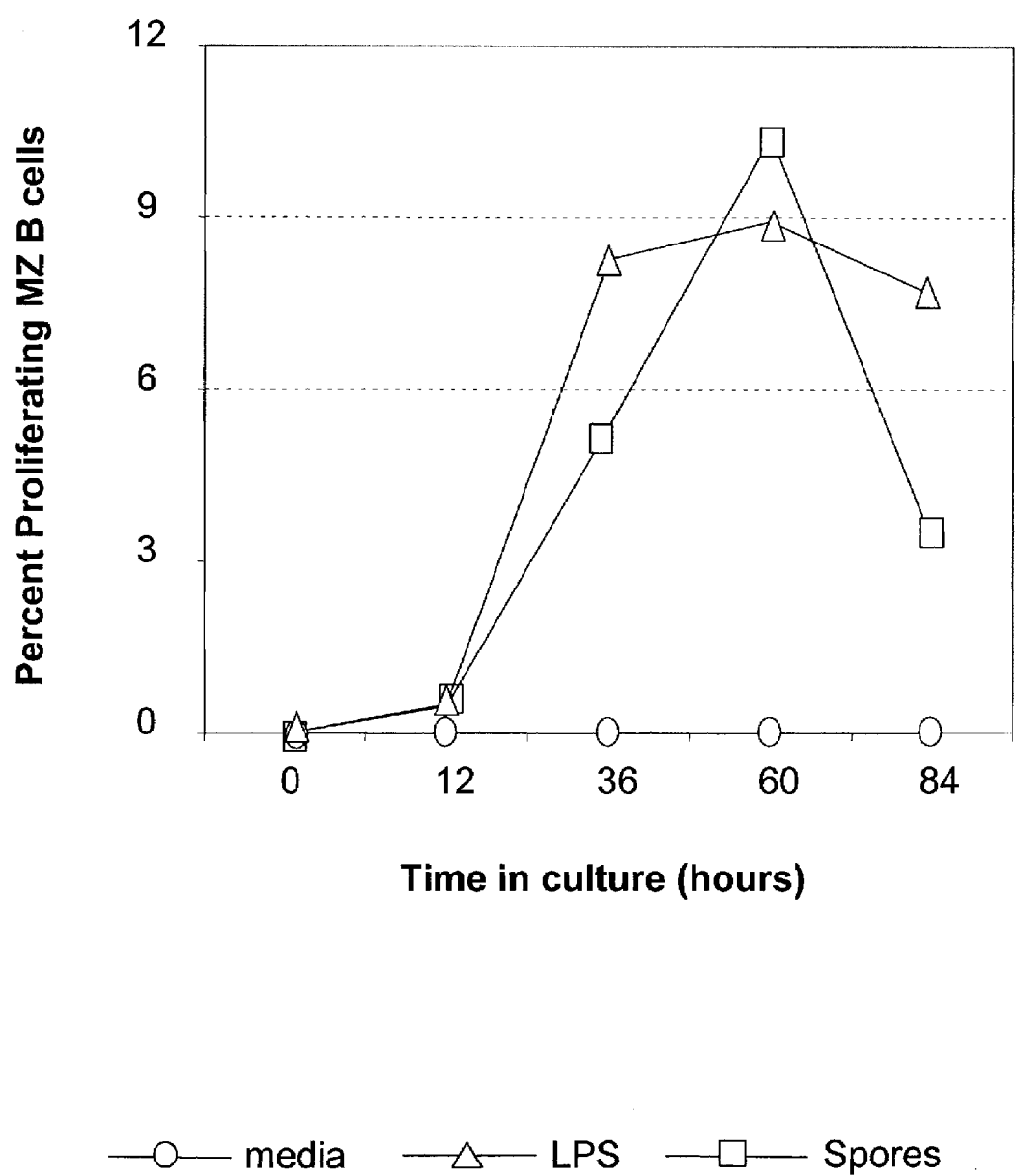

FIG. 17: Spores from *B. subtilis* induce proliferation in T-independent (innate) B-cells in vitro.

Splenocytes were cultured with either *B. subtilis* spores ($5 \times 10^7$), LPS (2 µg/ml) or media between 0 and 84 hours. Cells were removed and stained with the monoclonal antibodies, anti-HSA-FITC, anti-B220-CyChrome and anti-CD3, -CD4 and -CD8 conjugated APC. By flow cytometry the gated $B220^{+ve}$, $HSA^{low}$ and $CD3/4/8^{-ve}$ cells were analysed with respect to staining with DAPI. The data represents the proportion of proliferating T-independent Marginal Zone B-cells over time in responses to *B. subtilis* spores (squares), LPS (triangles) or media alone (circles).

Figure 18:
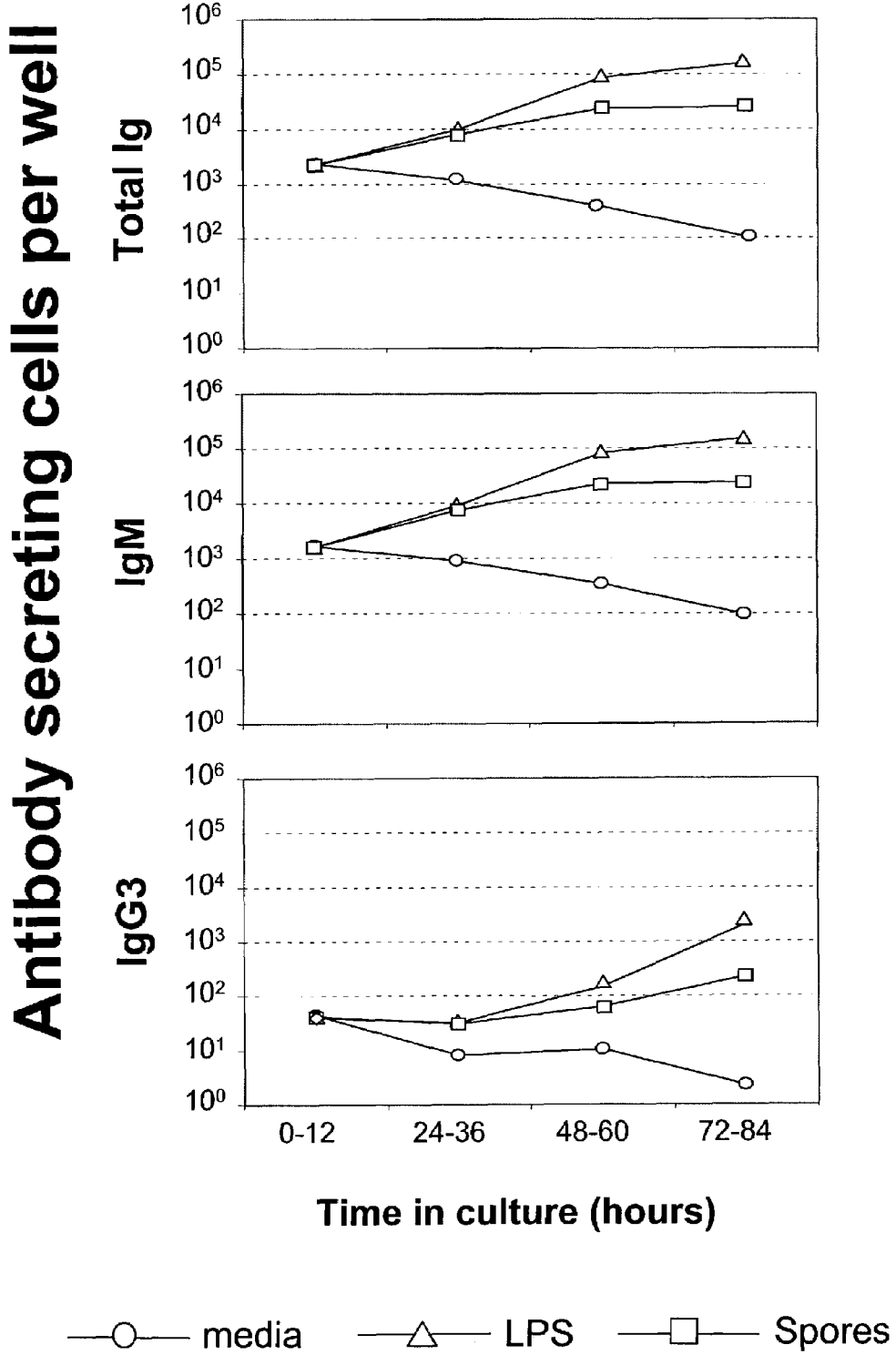

FIG. 18: Spores from *B. subtilis* induce innate antibody secretion by B-cells in vitro.

Splenocytes were cultured with either *B. subtilis* spores ($5 \times 10^7$), LPS (2 µg/ml) or media between 0 and 84 hours. The total number of Ig, IgM and IgG3 secreting B-cells present in splenic cultures was enumerated using a pan anti-Ig, IgM and IgG3 ELISPOT assay. The data represents the mean number of antibody secreting cells over time in responses to *B. subtilis* spores (squares), LPS (triangles) or to media alone (circles)

DETAILED DESCRIPTION OF THE INVENTION

We have demonstrated that spores from a well defined, genetically characterised strain of *B. subtilis* (168, ATCC number 23857; deposited Jul. 10, 1968 with the American Type Culture Collection (ATCC), 10801 University Blvd., Manassas, Va. 20110-2209, USA) can activate and mature murine bone marrow derived dendritic cells (BMDC) and also human dendritic cells in vitro, indicated by increased expression of cell surface activation markers (including co-stimulatory molecules) and by the production of interleukin-12 (IL-12) and tumour necrosis factor-α (TNF-α), followed (upon prolonged incubation) by production of IL-4. This data indicates that the spores stimulate dendritic cells to produce a balanced environment favourable to the activation of antigen specific T helper 1 (Th1 cells), responsible for initiating the cell-mediated arm of the immune response and also Th2 cells, responsible for initiating humoral immune responses. Thus spores as an adjuvant are significantly less likely to induce an allergic response to a co-administered vaccine component, which would be driven by a predominantly Th2 response.

We have also demonstrated that spores provide strong maturational stimuli to dendritic cells, such that these cells become efficient antigen presenting cells to prime both naïve, allogeneic and antigen-specific T cells. The relevance of these observations is that spores may be used as a maturational agent for dendritic cells exposed in vitro to tumour or infectious disease antigens in post-exposure therapy. The data also suggest spores may provide a highly effective adjuvant in the elderly, where depressed dendritic cell antigen presentation may require strong costimulatory/maturational signals and where decreased responsiveness to vaccination has been well documented (Spencer et al 1996, Manning et al 2001). For each of the above immunological parameters, we have achieved similar responses using human monocyte derived dendritic cells.

The invention uses spores from *B. subtilis* as an adjuvant by simple admixture with a candidate vaccine to boost the immune response to the vaccine components. Using tetanus toxoid (TT) as a model antigen, we have further demonstrated in mice that co-administration of spores with a sub-optimal dose of TT by the subcutaneous route is associated with a significant increase in the TT-specific T cell and antibody responses, compared to recipients of TT alone. Moreover, fine analysis of the antibody response, indicates that the spores stimulate the production of both classes of TT-specific IgG1 and IgG2a antibodies in a dose dependant manner. This is in contrast to alum or incomplete Freunds adjuvant, which skew the response to the IgG1 subclass. The relevance of these observations is that spores as an adjuvant also activate the Th1 arm of the immune response, responsible for providing "immunological help" to activate T cytotoxic lymphocytes (CTL), which are believed critical for the control and clearance of intracellular pathogens (eg. HIV, Mycobacteria tuberculosis, Hepatitis B, Hepatitis C, respiratory viruses etc.).

We have further demonstrated in mice that co-administration of spores with a sub-optimal dose of TT by the intranasal route enhances TT-specific IgA antibody producing cells in the upper respiratory tract and TT-specific IgG antibody producing cells in the draining lymph nodes. These observations indicate that the spores also act as a mucosal adjuvant (equal in potency to cholera toxin) to enhance both local immune responses (at the site of pathogen entry, as a first line defence) and also in the draining lymphoid tissues. Moreover, we have demonstrated that the adjuvant activity of the spore also enhances TT-specific secretory IgA responses in the vaginal tract, distal to the intranasal site of vaccine administration. The relevance of these observations is the identification of a new class of mucosal adjuvant, which is not based upon bacterial toxins or complex natural or synthetic molecules, which require extensive extraction and purification procedures.

We have also demonstrated that spores from *B. subtilis* enhance total serum IgG1 antibody following systemic administration and also enhance total IgA antibody in the upper respiratory tract following intranasal administration. These observations indicate that spores from *B. subtilis* may be used to enhance both local and systemic antibody production, in the absence of an immunogen, which may have relevance in boosting pre-existing immunity, for example a "travellers" vaccine or in boosting maternal immunity for passive transfer to babies who are almost entirely dependent upon antibodies from breast milk for protection against disease in the first six months of life.

Our observations also demonstrate that spores provide survival and maturational signals to B cells, including signals to upregulate surface MHC class II, which increase the ability of T helper dependent B cells to interact with T helper cells and generate high affinity antibody. These observations indicate the mechanism whereby spores act as an adjuvant to increase not only the magnitude but also the affinity of antibodies elicited to a vaccine or co-administered antigen.

The data herein also demonstrate that spores induce the proliferation, activation and secretion of IgM and IgG3 antibody by marginal zone B cells within a few hours of spore exposure. The relevance of these observations is the identification of an immunepotentiating activity of the spore, which induces "natural antibodies" from the evolutionary conserved marginal zone B cell repertoire, without any requirement for a specific antigen. This form of innate immunity is believed to be critical in the early control of pathogen replication and prevention of spread within a host. Mobilising innate immunity may prove critical in post exposure control during biological warfare or from travel or vacation acquired infection (particularly where the aetiology of the agent is unknown and rapid therapeutic intervention is required).

The Invention Has the Following Applications:

The maturation of dendritic cells (DC's) both ex vivo and in vivo, the relevance being to enhance the ability of DC's to optimally prime T cell responses. The inventors have shown that spores cause maturation of DC's. Since mature DC's are better at stimulating primary T cell responses, this property of the spore can be used when preparing DC's in vitro. Immature DC's can be used to take up antigen and then be treated with spores to mature the DC to a form that is more efficient at stimulating primary T cell responses. An example being administration of spore treated DC's into a patient as a therapeutic strategy in cancer or infectious disease. A further example being direct injection of spores into tumours, as a method to mature resident or infiltrating DC's to maximally present tumour antigens.

The invention also provides a method for spore treated DC's to produce IL-12, TNF-α and IL-4. The production of each cytokine by DC's is important to generate a balanced immune response. IL-12 production is critical in the generation of Th1 and CD8 cytotoxic T cell (CTL) responses and the production of IgG2a, IgG2b and IgG3 antibodies. IL-4 production stimulates Th2 responses and the production of IgG1 antibodies.

The property of the spore to stimulate DC's to produce high levels of IL-12 (and thus stimulate Th1 responses) can be used to treat, prevent, or ameliorate any suitable allergic reaction in combination with any suitable anti-allergenic agent. An allergy, in the context of the present invention, refers to an acquired hypersensitivity to a substance (i.e., an allergen). Allergic conditions include eczema, allergic rhinitis or coryza, hay fever, bronchial asthma, uticaria (hives), food allergies, and other atopic conditions. The list of allergens is extensive and includes pollens, insect venoms, animal dander, dust, fungal spores, and drugs (e.g., penicillin). Examples of natural, animal, and plant allergens can be found in International Patent Application WO 98/18810. The present inventive method can also be used to treat allergic asthma. Suitable anti-allergenic agents include those substances given in treatment of the various allergic conditions described above, examples of which can be found in the Physicians' Desk Reference (1998).

The property of the spore to more efficiently stimulate cell-mediated immune responses can be used as a method to administer spores with cancer vaccine components to treat any suitable cancer in combination with any suitable anti-cancer agent. Suitable cancers include cancers of the brain, lung (e. g., small cell and non-small cell), ovary, breast, prostate, and colon, as well as carcinomas and sarcomas. Preferably, the present inventive method is used to treat a solid tumour cancer. Suitable anti-cancer agents include those substances given in treatment of the various conditions described above, examples of which can be found in the Physicians' Desk Reference (1998).

The invention provides a method to enhance immune responses induced at mucosal surfaces i.e. to potentate induction of secretory IgA (and also IgG) antibodies elicited to vaccine components in mucosal secretions (nasal, pulmonary, vaginal, gastrointestinal and colostrum), with relevance to prevention/modulation of disease induced by pathogens transmitted across the body surfaces i.e. inclusive of but not restricted to respiratory, genito-rectal or enteric pathogens.

The invention also provides a method to enhance systemic immune responses generated to vaccine components i.e. potentate induction of immune responses elicited in secondary lymphoid tissues (cellular and humoral), with relevance to prevention/modulation of disease induced by blood borne or cutaneous transmitted pathogens or tumours in body tissues.

The invention provides a method of activating innate immunity, through two mechanisms. First, the action of the spore in stimulating IL-12 production by antigen presenting cells including the DC. The synthesised IL-12 triggers production of interferon-gamma and tumour necrosis factor (from natural killer cells, monocytes and macrophages) which provides resistance to microbial agents. The invention also provides a method for stimulating the expansion of splenic marginal zone B cells (and all T independent B cell sub-populations) and their rapid production of IgM and IgG3 (natural antibodies) from the evolutionary conserved B cell repertoire without specific knowledge of the infecting pathogen. This application has direct relevance as an immune stimulator administered against bacterial and non-bacterial exposure from germ warfare, where a rapid immune response against an unknown pathogen is required. A further application is as a generic therapeutic to stimulate innate immunity pre or neo exposure to common pathogens ie as a generic travellers or holiday vaccine.

The invention also provides a method of boosting pre-existing humoral immunity. An example would be for individuals previously immunised against specific pathogens (eg. cholera, typhoid, hepatitis B etc) where immunity is present although waning, and can be "topped up" in a generic antigen-independent manner by administration of a dose of spores in the absence of the vaccine component(s). Another example is a method for boosting existing maternal immunity for transfer across the placenta and also boosting IgA (and IgG) antibodies in breast milk without prior knowledge of the antigen and provide immunity to human neonates and infants and also pre-weaning livestock.

A further example is administering spores to stimulate immunity in hosts with ageing or immunocompromised immune systems. For example, to enhance local (secretory IgA) and systemic T cell and antibody (IgG, IgA and IgM) responses to vaccine components in the elderly and immuno-compromised individuals.

Suitable applications of each of the above examples include humans, livestock, companion animals, fish and poultry.

The invention also provides an adjuvant and delivery vehicle to boost the immune response elicited by plasmid DNA vaccines. The spores, when coated with the DNA vaccine, can be used as a delivery system to increase the uptake of the vaccine into dendritic cells. This can be done using poly L-lysine that can be directly conjugated to the surfaces of spores using standard conjugation techniques. Plasmid DNA can then be directly bound to the spore via the poly L-lysine. The length of the poly L-lysine chains can be varied for fast and slow release of the plasmid. By virtue of the spore's ability to mature the dendritic cell, this activity can enhance the ability of the dendritic cell to present antigens encoded by a DNA vaccine to T lymphocytes, resulting in an increased immune response. This embodiment of the invention could be highly relevant to vaccination not only against infectious diseases but also against tumours, which are invariably weakly immunogenic and require enhanced levels of co-stimulation provided by the antigen presenting cell to activate CD4 Th and CD8 cytotoxic T lymphocytes. An example would be the binding of a MUC1 expressing plasmid DNA onto the surface of poly L-lysine conjugated spores. The spores would be administered to an individual with a MUC1 expressing cancer (70% of all cancers express MUC1) via a parental route. It has been shown that vaccination against MUC1 has induced long-term suppression of tumour growth in a number of MUC1 expressing cancers (Johnen et al 2001).

The invention provides an adjuvant for use in human, livestock, companion animal, fish, & poultry vaccines.

Experimental verification of the advantages of the present invention is further described below and with reference to the accompanying Table and figure legends noted previously.

EXAMPLES

The following Examples are included to provide a more complete and consistent understanding of the invention described and claimed herein. The Examples do not limit the scope of the invention in any fashion.

Preparation of Spores for Use as Adjuvants

Bacillus sublilis strain 168 was cultured overnight at 37° C. on an agar plate from either a frozen glycerol stock of vegetative cells or from a frozen suspension of spores. A single colony was inoculated into 3 ml of Luria-Bertani (LB) medium and incubated at 37° C. in an orbital shaker until visible cell growth was seen (5-6 h). 1 ml of cell suspension was then inoculated into 250-300ml of Dulbeccos sporylation media (DSM) broth (in the absence of antibiotics) contained in a 2 liter baffled, sterile, flask and incubated for 30 hours at 37° C. in an orbital shaker. The crude spores were then pelleted by centrifugation (Sorvall GSA rotor; 5000 rpm, 10-15 minutes). The pellets were resuspended in 200 mls of sterile water and incubated 1-2 days at 4° C., to allow spores to mature and be released from mother cell sporangia. The mature spores were then pelleted by centrifugation (Sorvall GSA rotor; 5000 rpm, 10-15 minutes), resuspended in 40mls of phosphate buffered saline containing 250 μl of lysozyme (20 mg/ml) and incubated 1 h at 37° C. The spores were then re-pelletted by centrifugation (Sorvall GSA; 5000 rpm; 15 min.), washed in 40 mls of 1M sodium chloride, followed by further centrifugation (Sorval SS-34; 8000 rpm; 10 min). The spore pellets were then washed three times in double distilled water and re-centrifuged as indicated above. The spores were finally resuspended in 10 ml of sterile water and stored at −20° C. Spore concentration was enumerated by heating spore aliquots (65° C. for 1 hour) followed by serial dilution and spread on DSM agar plates. The plates were incubated for up to 2 days at 37° C. and the number of colony forming units (cfu) calculated. Spores were rendered germination deficient by heat treatment at 121° C. for 20 minutes at 20 atmospheres pressure.

Spores prepared as described above have been used in procedures described in the following Examples.

Example 1

Spores from Bacillus subtilis Activate Antigen Presenting Cells (APC)

Bone marrow-derived dendritic cells (BMDC) were isolated from Balb/c mice and cultured by standard procedures modified from Svensson et al 1997. Isolated bone-marrow derived (erythrocyte depleted) cells at $5 \times 10^6$ were cultured in RPMI medium supplemented with 10% foetal bovine serum (FCS) and 20 ng/ml recombinant Granulocyte-macrophage colony-stimulating factor (GM-CSF) (from R&D systems) on untreated plastic dishes. Non-adherent cells were removed on day 5 and CD11c+ dendritic cells (DC) were magnetically purified by positive selection on Magnetic activated cell separation (MACS) columns (Miltenyi Biotec GmbH) in accordance with manufacturer's instructions. Purified dendritic cells ($1 \times 10^6$ cells/ml) were incubated in 24-well tissue culture plates with either $10^5$, $10^6$, or $10^7$ autoclaved (replication defective) B. subtilis spores or with lipopolysaccharide (LPS from E. coli) at 2 μg/ml or with tissue culture media as a control for 12-18 hours at 37° C. in 5% $CO_2$. The cells were then washed three times in RPMI by centrifugation (1,600 rpm for 5 minutes at 4° C.), resuspended in fresh medium and then kept on ice prior to staining for cell surface markers, cytokines or functional assays.

To determine activation of the BMDC by B. subtilis spores, flow cytometry was used to quantitate expression of cell surface Major Histocompatibility complex (MHC) class II and costimulatory molecules following incubation of bone marrow derived dendritic cells in the presence or absence of spores. The cells were incubated 30 mins on ice with anti-mouse CD32/CD16 (Fc II/III receptor block, Pharmingen) at $10^6$ cells in 50 µl flow cytometry buffer (phosphate buffered saline containing 2% foetal bovine serum and 5 mM disodium ethylene diamine tetraacetate [EDTA]).

The cells were then incubated (1 hour on ice) with either anti-mouse Phycoerythrin conjugated CD11c (1/100), anti-mouse fluoroscein-isothyocyanate conjugated B220 (1/200) or with biotinylated anti-MHC class II, anti-CD86, anti-CD40 or anti-CD11b monoclonal antibodies (all diluted 1/200). BMDC were also stained with T-cell markers to determine purity. After thorough washing (3×), the cells were stained with biotinylated monoclonal antibodies and were subsequently incubated 40 mins on ice with streptavidin conjugated-Phycoerythrin-Cytochrome 5 (1/200). All antibodies were purchased from Pharmingen (USA). The cells were re-washed (3×), fixed in 1% formyl saline and analysed by flow cytometry (EPICS XL Beckman Coulter). The data as shown in FIG. 1 clearly indicate that spores activate bone marrow derived dendritic cell cultures in a dose dependant manner. Incubation of BMDC with spores led to a significant increase in the percentage of cells expressing high levels of MHC class II and the co-stimulatory molecules CD86 and CD40 in a dose dependent manner. Furthermore, the mean fluorescent intensity (MFI) of the cells also increased in a dose dependant manner (data not shown). Thus B. subtilis spores induce a rapid and potent up-regulation of MHC class II and costimulatory molecules on antigen presenting cells. The implications from these observations are that these treated BMDC express the full complement of cell surface co-stimulatory and activation molecules required to achieve the full activation of T cells (see Example 3)

Example 2

B. subtilis Spores Activate Human Monocyte Derived Dermal Dendritic Cells and Langerhans Cells.

Generation of Human Monocyte Derived Dermal Dendritic cells:

Peripheral blood mononuclear cells (PBMCs) from healthy uninfected volunteers were initially separated from heparinised whole blood using Histopaque 1077 (Ficoll). Monocytes were harvested from the interface of a 50% Percoll gradient after centrifugation of PBMCs at 300 g for 30 minutes. The cells were washed in HEPES buffered RPMI-1640 medium supplemented with 2% foetal calf serum (FCS), 1% Penicillin, 1% Streptomycin and 1% L-glutamine (defined as RPMI complete medium). After 2 hours incubation in an atmosphere of 5% $CO_2$ at 37° C. with RPMI complete medium supplemented with 10% FCS in gelatine-coated flasks, the adherent cells were gently washed and resuspended in 1000 IU/ml Interleukin-4 (IL-4) and Granulocyte Macrophage-Colony Stimulating factor (GM-CSF) at 150 IU/ml and incubated for 7-10 days. At day 2, IL-4 and GM-CSF (as previously described) were added directly to the flasks. At day 4-5, cells were washed, resuspended into fresh complete media containing IL-4 and GM-CSF (as indicated above) and transferred into 24-well plates at a concentration of $5 \times 10^5$ cells/mi/well. At days 7 and 9, half of the media was removed and replenished with fresh complete media containing IL-4 and GM-CSF.

Dermal dendritic cells, (DDC's) at $1 \times 10^6$ cells/ml were incubated in 24-well tissue culture plates with either $10^5$, $10^6$, or $10^7$ autoclaved (replication defective) B. subtilis spores, culture media alone or with lipopolysccharide (LPS) from E.

coli at 1 µg/ml. The cells were then cultured for 48 hours at 37° C. in 5% $CO_2$. The cells were then washed three times in RPMI by centrifugation (1,600 rpm for 5 minutes at 4° C.), resuspended in fresh medium and then kept on ice prior to staining for cell surface markers. The cells were stained for CD14, E-cadherin, CD1a and CLA to confirm their DDC phenotype and for the activation markers HLA-DR (human MHC class II), CD80, CD86 and CD83. The stained cells were then analysed by flow cytometry as in Example 1.

The data shown in FIG. 2 and summarized in Table 1, indicate that the derived cell population were CD14 negative, high in CD1a but low in E-cadherin and CLA expression, confirming their DDC phenotype.

The addition of spores to cultures of human DDCs was associated with their activation and maturation, as shown by the cell surface upregulation of HLA-DR, CD80, CD86 and CD83 compared to cells incubated with the media alone, as shown by the increase in the Mean Fluorescence Intensity (MFI) for each cell surface marker (FIG. 2 and Table 1). The level of DDC activation associated with the spores was comparable to the levels induced by the well-studied mitogen, LPS, included as a positive control. An increase in HLA-DR and CD86 expression has also been observed following incubation of human Langerhans dendritic cells (data not shown). These results indicate that human antigen presenting cells (Dermal and Langerhans dendritic cells) respond to spores in a highly similar manner to murine BMDC's.

TABLE 1

B. subtilis Spores Activate Human Monocyte Derived Dermal Dendritic cells

|  | Negative control | | LPS 1 ug/ml | | Spores 10 | |
| --- | --- | --- | --- | --- | --- | --- |
|  | % | MFI | % | MFI | % | MFI |
| CD14 | 1 | 0.07 | <IC | <IC | <IC | <IC |
| E-CD1a | 6.8 | 1.3 | 2 | 1.2 | 3.1 | 1 |
| CD1a | 73 | 33 | 70 | 20 | 70 | 27 |
| CLA | 12 | 2 | <IC | <IC | <IC | <IC |
| HLA-DR | 90 | 60 | 96 | 283 | 93 | 139 |
| CD80 | 54 | 11 | 84 | 28 | 72 | 18 |
| CD86 | 83 | 87 | 95 | 473 | 90 | 215 |
| CD83 | <IC | <IC | 87 | 16 | 47 | 11 |

The percentage of positive cells was determined by subtraction of the percent staining detected from isotype matched control antibody from specific staining detected with each monoclonal antibody. The MFI value refers to the mean florescent intensities associated with the positively stained cells. <IC refers to when the specific staining gave values less than the isotype control.

Example 3

Spores from B. subtilis Stimulate Antigen Presenting Cells to Secrete Cytokines.

Activated dendritic cells often demonstrate an enhanced capacity to secrete inflammatory cytokines, which provide environmental signals to polarise responding naïve T cells and influence the type of immune response elicited to an antigen. We therefore examined, by intra-cellular cytokine staining, whether treatment of BMDC with spores led to cytokine production. BMDC cultured in the presence or absence of 5 spores per cell for 12 or 36 hours, and were subsequently incubated for a further 6 hours with brefeldin A (10 µg/ml). The cells were then fixed in 1% formyl saline for 15 minutes at room temperature, washed with flow cytometry buffer and then permeabilised (15 minutes at room temperature) with phosphate buffered saline containing EDTA, 2% foetal calf serum and 0.2% saponin. The cells were then washed 3× with flow cytometry buffer, blocked with anti-mouse CD32/CD16 (Fc 11/1111 receptor block, Pharmingen, described above) and then incubated with PE-conjugated monoclonal antibodies to either interleukin (IL) -2, IL-4, IL-10, IL-12, TNF-α or interferon-gamma (IFN-γ), all antibodies from Pharmingen, diluted ½₀₀ in flow cytometry buffer. The BMDC were incubated for 1 hour at room temperature, washed 3 times in flow cytometry buffer and then fixed with 1% formyl saline, followed by flow cytometric analysis (EPICS XL Beckman Coulter).

Our results (Table 2) demonstrate that treatment of BMDC with spores (after 12 hours of stimulation) led to an increase in the percentage of IL-12 and TNF-α expressing cells (17.9% and 42% respectively) compared to control, non-activated BMDC (1.9% and 2.0% respectively). Following 36 hours of culture, a significant increase in IL-4 expressing BMDC was observed from the spore stimulated cultures (23%) compared to unstimulated control cultures (3.4%). The expression of IL-12 and IL-4 followed closely the temporal pattern of cytokine expression reported previously by antigen activated DC (Langenkamp et al 2000 and Morelli et al 2001). IL-12, TNF-α and IL-4 production showed a dose-dependent correlation to increasing spore concentration (data not shown). No differences in IL-2, IL-10 or IFN-γ expressing cells were detected. The data indicate that murine BMDC activated with spores produce both Th1 (IL-12) and Th2 (IL-4) polarising cytokines associated with a balanced immune response. The implications from these observations are that these

TABLE 2

B. subtilis Spores Induces TNF α, IL-12 and IL-4 Expression in Bone-Marrow Derived Dendritic cells

| | Percentage positive cells by flow cytometry | | | |
|---|---|---|---|---|
| | 12 hours post stimulation | | 36 hours post stimulation | |
| Cytokine | Unstimulated | Spore MOI 5 | Unstimulated | Spore MOI 5 |
| IL-2 | 0.44 | 0.24 | 0.37 | 0.4 |
| IL-4 | 0.38 | 0.4 | 3.4 | 23.0 |
| INF-γ | 0.3 | 0.47 | 0.12 | 0.07 |
| IL-10 | 0.56 | 0.36 | 0.3 | 0.14 |
| IL-12 | 1.9 | 17.9 | 0.34 | 0.15 |
| TNFα | 2.0 | 42 | 0.2 | 0.8 |

The percentage of positive cells was determined by subtraction of the percent staining detected from isotype matched control antibody from specific staining detected with each anti-cytokine monoclonal antibody. Data significantly above background are highlighted in bold.

treated BMDDC may have a role in cytotoxic T lymphocyte (CTL) development. Firstly, the phenotype of the spore treated BMDDC was comparable to published phenotypes of splenic DC which have been shown to prime CTL in vivo (Reis e Sousa et al 1997) suggesting that spore treated DC may be capable of priming CTL. Moreover, MHC class I, CD40 and CD86 expression was increased which is consistent with current knowledge that increased expression of these cell surface molecules is essential to prime for CTL. Secondly, spores induce IL-12 production by DC, driving a Th1 cytokine profile, which is essential for inducing CTL responses. Thus these observations suggest a pre-disposition of spore treated DC to prime for CTL responses.

Example 4

B. subtilis Spores can Stimulate Cellular Proliferation in Naïve Splenocytes.

To determine whether the spore activated antigen presenting cells would also demonstrate an increase in functional activity, we investigated the ability of Antigen presenting cells to induce proliferation in naïve T-cells. Single cell suspensions of erythrocyte depleted splenocytes (derived from Balb/c mice) were incubated at $5 \times 10^5$ cells in 100 μl of RPMI medium (containing 10% foetal calf serum) in 96 well microtitre plates. Triplicate wells were co-incubated with either $5 \times 10^6$, $5 \times 10^5$, $5 \times 10^4$, or $5 \times 10^3$ replication deficient B. subtilis spores (equivalent to a multiplicity of infection [MOI] of 10, 1, 0.1 and 0.001 respectively) in a further 100 μl of serum free medium or with the T cell mitogen Concanavalin A (Con A at 1 μ/ml) or media alone. After 3 days at 37° C. in 5% $CO_2$, cultures were incubated with 0.8μ Ci of $^3$[H] thymidine (Amersham) for 12 hours and harvested onto nitrocellulose filters, dried and the radioactivity incorporated determined by scintillation counting (Packhard, Topcount). Co-incubation of naïve splenocytes with spores led to a significant level of cellular proliferation in a dose related manner as shown in FIG. 3. Similar data has been achieved using human monocyte derived dendritic cells (not shown). The observed proliferation of naïve T cells by dendritic cells exposed to spores is consistent with spore driven dendritic cell maturation and cytokine production inducing clonal T cell proliferation and differentiation.

Example 5

B. subtilis Spore Activated Antigen Presenting Cells are Functional and Enhance the Stimulation of Antigen-Specific T Cells.

To determine whether the proliferative effect observed with a mixed haemopoetic cell population of splenocytes was due to activation of Antigen presenting cells present in the culture, proliferation assays were performed on T cell enriched splenocytes co-incubated with spore activated BMDC. Cultures of 5 day old BMDC were established (as described previously) and incubated for 12 hours (at 37° C. in 5% $CO_2$) in culture medium (RPMI supplemented with 10% foetal calf serum, L-glutamine, penicillin and streptomycin) containing replication deficient B. subtilis spores at a ratio of either 5, 0.5 or 0 spores per dendritic cell.

The cultures were then washed 3× in culture medium and maintained on ice until co-cultured with naïve spleen derived T cells. Suspensions of erythrocye depleted splenocytes were enriched for T cells by passage through two nylon wool columns (Mishell and Shiji, 1980). T-cell enriched splenocytes ($2 \times 10^5$/well) were cultured in quadruplicate in 96 well microtitre plates with irradiated (2500 rad) BMDC (previously incubated with either 5, 0.5 or 0 spores/cell) at a T-cell to BMDC ratio of either 10:1, 20:1, 40:1 or 80:1 which is equivalent to $2 \times 10^4$ $1 \times 10^4$, $5 \times 10^3$ or $2.5 \times 10^3$ BMDC/ well). After 3 days (at 37° C. in 5% $CO_2$), 0.8μ Ci of $^3$[H] thymidine (Amersham) was added to the cultures, incubated for 12 hours and incorporated radioactivity evaluated as described previously. The results clearly demonstrate that spore activated BMDC induce proliferation of T-cell enriched splenocytes in a dose dependant manner, as shown in FIG. 4a. Non-activated BMDC showed low ability to induce the proliferation of enriched T cells. However prior activation of BMDC with *B. subtilis* spores led to strong T cell stimulation, which was significant (p=0.00015 and p=0.00025 by ANOVA) for BMDC stimulated with 5 or 0.5 spores/cell compared with non-activated control BMDC at a 10:1 T cells to BMDC ratio. In the absence of antigen presenting cells, the spores failed to induce proliferation of T-cell enriched splenocytes (data not shown). Therefore we have demonstrated that antigen presenting cells are required for the spore induced proliferation of splenocytes, and that spore stimulated BMDCs (ie in. vitro generated antigen presenting cells) induce profound proliferation in these otherwise non-proliferating cultures.

Example 6

Spores from *B. subtilis* Spore Activate Both Human and Murine Dendritic Cells to Induce Proliferation of Allogeneic T Cells.

The ability of DC's to enhance the proliferation of allogeneic T cells in vitro has been established by immunologists as a robust functional readout for DC maturation and activation. To address the ability of spore activated DC's to induce proliferation of allogeneic T cells, immature dendritic cells were grown up from murine BALB/c (H-2d) bone marrow or human blood monocytes as described in examples 1 and 2 respectively. The DCs were then incubated with, either 10, 1, 0.1 or 0 germination deficient spores per DC for 12 hours (at 37° C. in 5% $CO_2$) in culture medium (RPMI supplemented with, L-glutamine, penicillin and streptomycin and either 10% foetal calf serum or 10% autologous serum for the mouse and human DCs respectively). The murine BMDCs were mixed with splenic T-cells from either DBA (H-$2^k$) or C57BL/6 (H-2b) mice for 4 days (as described in example 5. The human DDCs were cultured likewise for 5 days with human T-cells from an allogeneic donor. Proliferation was measured by $^3$[H]-thymidine incorporation (also described in example 5). Both the mouse and the human spore activated DCs induced significantly higher levels of proliferation in the allogeneic T-cells than the unpulsed DCs (see FIGS. 4b and 4c). The increased proliferation was dose dependent on the number of spores incubated with the DCs.

This data clearly demonstrates the ability of *B. subtilis* spores to activate human and murine DC cells to greater functionality in the stimulation of T-cells.

Example 7

*B. subtilis* Spores Stimulate Systemic T-Cell Responses to Vaccine Antigens

The potential of *B. subtilis* spores to act as an adjuvant in vivo and augment antigen specific immune responses was tested by subcutaneous immunisation of Balb/c mice (5 per group) on days 0, 14 and 28 with phosphate buffered saline containing either 50 µg of tetanus toxoid (TT, Pasteur Merrieux Conought), $5 \times 10^8$ *B. subtilis* spores, or 50 µg TT with either $5 \times 10^6$, $5 \times 10^7$ or $5 \times 10^8$ *B. subtilis* spores. Immunised and naïve mice were euthanized on day 42.

For evaluation of antigen specific T cell proliferation, splenocytes were selectively lysed for erythrocytes and then were cultured in quadruplicate for 3 days (as previously described) in the presence of either TT (50, 20, 10, 1 or 0.2 µg/ml) or germination deficient *B. subtilis* spores ($2 \times 10^7$, $2 \times 10^6$, $2 \times 10^5$, $2 \times 10^4$, $2 \times 10^3$). Positive and negative controls included ConA (2 µg/ml) and media respectively. Cultures were incubated with $^3$[H] thymidine (Amersham) for 12 hours and incorporated radioactivity evaluated as described previously. The results clearly demonstrate that co-inoculation of spores with an immunogen enhances cellular proliferative responses to the target antigen (in this case TT), where inoculation of the target antigen alone failed to induce a significant response, p=<0.005 by ANOVA (FIG. 5).

Example 8

*B. subtilis* Spores Augment Antibody Responses to Vaccine Antigens.

To determine whether *B. subtilis* spores could enhance antibody responses to target antigens, spores were administered by the subcutaneous route (according to the protocol described in Example 7) in the presence of a sub-optimal dose of TT (5 µg) and boosted with the same dose of TT and spores on day 14 by the intraperitoneal route. Mice were euthanized on day 35. Blood samples were collected pre, 7 days post each immunisation and at euthanization.

The presence of TT-specific total Immunoblobulin (Ig) and IgG1 or IgG2a subclass antibodies in serum were measured by standard Enzyme linked immunoassay (ELISA) using TT or an alkali extract of *B. subtilis* spore coat proteins as the capture antigen. Immulon-4 96 well plates (Dynex Technologies) were incubated with 100 µl of either TT protein (10 µg/ml in phosphate buffered saline, pH 7.4) or alkali extracted *B. subtilis* spore coat proteins (10 µg/ml in carbonate buffer pH 9.5) O/N at 4° C. The plates were then washed 5 times with ELISA buffer (phosphate buffered saline pH 7.4 containing 0.1% Tween 20). The plates were blocked with ELISA buffer containing 4% normal goat or horse serum. Test sera were diluted in 4% normal horse serum in serial two fold dilutions from 1:100, then incubated on antigen coated plates for one hour at room temperature. The plates were washed 5 times with ELISA buffer and then incubated with 100 µl of either horseradish peroxidase conjugated anti-mouse Ig, anti-mouse IgG1 or anti-mouse IgG2A antibodies (Southern Biologicals) diluted 1/2000 in ELISA buffer for 1 hour at room temperature. The plates were then washed 6 times in ELISA buffer and 200 µl of O-phenylenediamine dihydrochloride (OPD, Sigma substrate kit) was added to each well and the optical density at 450 nm recorded.

The results were expressed as the lowest dilution of serum giving an optical density value (OD) value of 0.1 units above the mean OD value of the cognate pre-immune serum. The results clearly indicate that co-administration of spores (at each dose) with an antigen significantly augmented the total serum immunoglobulin response to a target antigen, p<0.05 by ANOVA for each dose of spores administered (FIG. 6). Furthermore, both IgG2a as well as IgG1 antibodies were induced to the target antigen. The increase in serum TT-specific IgG2a antibody was positively related to the administered spore concentration, whereas immunisation with TT alone produced almost exclusively an IgG1 antibody response (FIG. 6). This is clearly illustrated by FIG. 7, which demonstrates that the high ratio of TT-specific IgG1:IgG2a antibody elicited by immunisation with TT alone (221:1) is decreased to 13:1 at the highest inoculated spore dose. Indicating that *B. subtilis* spores facilitate augmentation of a balanced IgG1/IgG2a antibody response. Although IgG responses are induced to the spore, this response was much lower than to the co-administered TT (data not shown). This suggests that the adjuvant activity of the spore to augment the immune response generated against a target antigen exceed the immunogenicity of the spore itself.

Example 9

B. subtilis Spores Augment Local Mucosal Antibody Responses to a Vaccine Antigen Following Mucosal Administration Balb/c mice (5 per group) were inoculated on days 0, 14 and 28 via the intra-nasal (in) route with either: 10 µg TT, $5\times10^8$ B. subtillis spores, or 10 µg TT co-administered with either $5\times10^6$, $5\times10^7$ or $5\times10^8$ B. subtilis B. subtilis spores or 2 µg cholera toxin (CT). Naïve mice were included as a negative control. Vaginal washings, $2\times50$ µl were taken at day −3, −1, 21 and 35. The mice were tail bled at day −2 and 24. Blood, cervical lymph nodes (CLN) and nasal associated lymphoid tissue (NALT) were removed at termination (day 42) to enumerate TT-specific antibody secreting B cells by enzyme linked immunosorbent spot forming assay (ELISPOT) and TT-specific antibodies by ELISA.

ELISPOT plates (Millipore, MAHAS4510) were coated with either TT (10 µg/ml), Ovalbumin (10 µg/ml), goat anti-mouse IgA, or goat anti-mouse IgG to determine antigen specific or total IgA and IgG antibody secreting B-cells. The plates were then incubated for 24 hours at 4° C. and washed 6 times with sterile phosphate buffered saline. The plates were then blocked with tissue culture medium (RPMI+10% FCS) for 1 hour at 37° C.+5% $Co_2$. Lymphocytes (containing antibody secreting B cells) were isolated from nasal tissue (NALT) by tissue disruption, followed by digestion with collaginase (10 mg/ml) for 1 hour at 37° C. and purification over a Percol separation gradient. 100 µl of serially diluted lymphocytes (from $10^6$ cells/ml) were added to duplicate ELISPOT wells and incubated for 12 hours at 37° C.+5% $CO_2$. The plates were then washed 5 times with ELISA buffer (as described in Example 6) and blocked overnight with ELISA buffer containing 5% normal goat serum. The block was removed and either peroxidase conjugated goat anti-mouse IgG or IgA (1/2000 diluted in ELISA buffer) was added (100 µl/well). The plates were incubated for 2 hours at room temperature and then washed 6 times (as described above). The plates were then developed (15 minutes) with 3,3,5, tetramethylbenzidine (TMB-peroxidase substrate, Vector laboratories), washed 6 times with water and dried. TT-specific and total IgA and IgG spots were enumerated using a light-dissecting microscope.

The results demonstrate that co-administration of B. subtilis spores with TT was associated with a spore dose dependent increase in the number of TT-specific IgA secreting B cells present in nasal associated lymphoid tissue of the vaccinated animals (FIG. 8). The number of B-cells secreting TT-specific IgA increased from 15 spot forming cells per mouse (TT only group) to over 200 spot forming cells per mouse for TT-specific IgG secreting B cells in the nasal associated lymphoid tissue of the vaccinees. Co-administration of TT with $5\times10^8$ B. subtilis spores elicited 87.5 TT-specific IgG spot forming cells per mouse, compared to zero detected in mice inoculated with TT alone (data not shown). The data indicate that spores augment the immunogenicity of mucosally administered TT, thus B. subtilis spores exhibit mucosal adjuvanticity for co-administered antigens.

Example 10

Mucosal Delivery of B. subtilis Spores Augments Antibody Responses to Vaccine Antigens at the Local Draining Lymph Nodes.

Lymphocytes isolated from the cervical lymph nodes (CLN) from each of the vaccinated groups described in Example 9 were analysed by ELISPOT assay for TT-specific IgG secreting B-cells (as described in Example 7). Co-administration of $5\times10^8$ B. subtilis spores with TT was associated with an eight-fold (or greater) increase in the number of TT-specific IgG secreting B cells as compared with TT alone (FIG. 9). This result was also reflected in the serum levels of TT-specific antibody. Following the final immunisation, recipients of TT and B. subtilis spores (at each dose) demonstrated a 10-fold or greater TT-specific serum IgG antibody titre than recipients of TT alone (data not shown).

Example 11

Intranasal Delivery of B. subtilis Spores Elicits Genital Mucosal Antibody Responses to Vaccine Antiiens TT-specific IgA present in vaginal secretions from each of the vaccination groups (described in Example 9) was evaluated by ELISA as previously described. The end point antibody titre was defined as an optical density reading of 0.1 (as determined by 3× the optical density reading above the background pre-immune serum sample). Co-administration of TT with B. subtilis spores by the intranasal route, was associated with a significant increase in the TT-specific IgA titre detected in vaginal fluids, compared to recipients of TT alone, who demonstrated no detectable TT-specific IgA. (FIG. 10). The increase in TT-specific IgA in vaginal fluid was spore dose related. At a dose of $5\times10^8$ B. subtilis spores, the TT-specific IgA response demonstrated in vaginal fluid was greater than that detected in recipients administered TT adjuvanted with Cholera toxin by the intranasal route. Thus germination deficient spores of B. subtilis also act as an adjuvant to enhance antigen-specific IgA responses at mucosal sites distal to the site of vaccine delivery

Example 12

Systemic Delivery of B. subtilis Spores Enhances Total Serum IgG1 Antibody Levels The total serum levels of IgG1 and IgG2a antibody were determined by radial immunodiffusion assay according to the manufacture's instructions (The Binding Site, UK) from mice in each of the sub-cutaneous vaccination groups, described in Example 8. Both pre and post vaccination sera from each group were analysed. An 8 to 10 fold increase in post vaccination total serum IgG1 antibody (relative to the pre-immune serum) was associated with systemic delivery of B. subtilis spores (FIG. 11). The significant increase in mean total serum IgG1 could not be accounted for by the spore specific IgG1 response. Moreover, the elevation in serum IgG1 was specific, since serum levels of IgG2a were comparable pre and post vaccination (data not shown). These observations demonstrate that spores from B. subtilis act as a polyclonal activator of IgG1 secreting B cells.

Example 13

Mucosal Delivery of B. subtilis Spores Enhances Total IFA Antibody Secreting Cells in the Upper Respiratory Tract Polyclonal activation of IgA secreting B cells was also demonstrated by ELISPOT assay from lymphocytes isolated from the nasal tissue of mice following intranasal administration of B. subtilis spores (Example 9). A greater than ten fold increase in total IgA secreting B cells was observed at a dose of $5\times10^8$ spores (greater than 800 IgA spot forming cells per nasal tissue) compared with naïve mice (80 spot forming cells per nasal tissue), as illustrated in FIG. 11. The increase in total IgA secreting B-cells correlated positively with dose of *B. subtilis* spores. No significant difference in IgG secreting B cells was observed in nasal tissue (data not shown). Thus *B. subtilis* spores can act as a polyclonal stimulator of both locally secreted IgA at the mucosal epithelia and also of IgG1 subclass antibody in serum.

Example 14

*B. subtilis* Spores Provide Naïve and Primed B Cells with Survival and Maturational Signals.

Duplicate splenocyte cultures (5×10⁶ cell/ml) were established from C56BL/6 mice and cultured in RPMI+10% FCS at 37° C. with either 5×10⁷ *B. subtilis* spores or LPS (2 μg/ml) and compared to media alone. At sequential time points, cells were removed, stained with the following antibodies (anti-HSA-FITC, anti-IgD-PE, anti-MHC class II-ECD, anti-B220-CyChrome and APC-conjugated anti-CD3, -CD4 and -CD8) and then analysed by flow cytometery. T-cells were gated on using the T-cell markers CD3, CD4 and CD8. B-cells were collectively gated using B220. The different B-cell sub-populations were gated on using the markers B220, HSA and IgD. Naive T-dependant B-cells were defined as B220$^{+ve}$ HSA$^{low}$ IgD$^{+ve}$, whereas primed T-dependant B-cells were defined as B220$^{+ve}$ HSA$^{low}$ IgD$^{-ve}$. The innate T-independent B-cell population (known as Marginal zone or MARGINAL ZONE B-cells) were defined as B220$^{+ve}$ HSA$^{high}$ IgD$^{-ve}$. The gated T-dependant B-cell population (naïve and primed) were analysed by foreword and side scatter and surface expression of IgD. Foreword and side scatter pertains to the size and shape of the B-cells and can be used to distinguish live from dead and blasted from non-blasted cells. Incubation of T-dependant B-cells with *B. subtilis* spores increased their survival in culture (see FIG. 13) indicating the ability of the spores to generate survival stimuli for T-dependent B-cells. Furthermore, naive T-dependent B-cells reduced their surface expression of IgD (see FIG. 14) demonstrating the ability of spores to mature naive B-cells. These results demonstrate a mechanism by which spores act as a potent adjuvant to enhance the initial priming of B cells. This mechanism being via the enhancement of longevity and maturation of naive B-cells.

Example 15

*B. subtilis* Spores Upreiulate MHC Class II on B Cells

Splenocyte cultures were established and labelled with flurochrome-conjugated antibodies as previously described in example 14. The level of surface MHC class II was demonstrated to be increased for each B-cell sub-population cultured in the presence of spores (as shown in FIG. 15). The relevance of this observation relates directly to the adjvanticity of the spore to boost immune responses to specific vaccine antigens. T-cell dependent B-cells generate high affinity antibodies to vaccine/tumour antigens. Thus spore induced upregulation of MHC class II increases the ability of T-cell dependant B-cells to interact with T-helper cells and so enhances their ability to generate T-dependant high affinity antibodies.

We have also demonstrated that surface MHC class II was unregulated on T-independent B-cells. This B cell sub-population demonstrates potent antigen presenting activity. Upregulation of MHC class II on Marginal Zone B cells also increases their ability to stimulate T-helper responses to a vaccine/tumour antigen, which in turn can then provide greater help for the T-dependant B-cells. This data provides direct evidence of multiple mechanisms by which *B. subtilis* acts as an adjuvant to boost both B-cell and also T-cell responses in vivo.

Example 16

*B. subtilis* Spores Induce Blasting, Proliferation, Activation and Rapid IgM Secretion by Marginal Zone B Cells.

Splenocyte cultures were established and labelled with flurochrome-conjugated antibodies as previously described in example 14. The T-independent B-cells were gated and analysed by foreward and side scatter. The results clearly demonstrate that *B. subtilis* spores induce blasting (a measure of cellular activation) of the Marginal zone B-cells (as shown in FIG. 16). The stained B-cells were further fixed with 1% paraformaldehyde, permeabilised with 0.2% saponin and then stained with DAPI (1 μg/ml). This technique allows quantification of the amount of DNA present within each cell and hence the number of cells undergoing division. The data clearly shows that spores induce significant proliferation in the Marginal Zone B-cell population (see FIG. 17).

To determine the consequences of spore induced activation of the Marginal Zone B-cell population, immunoglobulin synthesis (total Ig, IgM and IgG) was measured (by ELISPOT assay) from cultures used for the staining experiments. The results clearly demonstrate that spores induce a greater than 10 fold increase in the number of antibody secreting B-cells within the cultures. The increase in antibody production was predominantly IgM but also IgG3 (as shown in FIG. 18). These results demonstrate a mechanism whereby *B. subtilis* spores activate Marginal Zone B-cells and their rapid induction of natural antibody secretion. This discovery pertains directly to the potential of *B. subtilis* spores to act as a booster of natural antibodies which provide protection against bacterial and non-bacterial pathogens in the absence of prior pathogen exposure or vaccination. This rapid induction of antibody could be utilized in limiting the spread of bacterial or non-bacterial infection in the first 12-36 hours following exposure to an unknown agent(s). Mobilising innate immunity may prove critical in post exposure control during biological warfare or by travel or vacation acquired infection (particularly where the aetiology of the agent is unknown and rapid therapeutic intervention is required)

Some further examples of the components of vaccine compositions in accordance with the present invention are listed below.

Examples of viral antigenic and immunogenic polypeptides include, but are not limited to, adenovirus pglypeptides, alphavirus polypeptides, calicivirus polypeptides, e.g., a calicivirus capsid antigen, coronavirus polypeptides, distemper virus polypeptides, Ebola virus polypeptides, enterovirus polypeptides, flavivirus polypeptides, hepatitis virus (A to E) polypeptides, e.g., a hepatitis B core or surface antigen, herpesvirus polypeptides, e.g., a herpes simplex virus or varicella zoster virus glycoprotein, immunodeficiency virus polypeptides, e.g., the human immunodeficiency virus envelope or protease, infectious peritonitis virus polypeptides, influenza virus polypeptides, e.g., an influenza A hemagglutinin, neuraminidase, or nucleoprotein, leukemia virus polypeptides, Marburg virus polypeptides, orthomyxovirus polypeptides, papilloma virus polypeptides, parainfluenza virus polypeptides, e.g., the hemagglutinin/neuraminidase, paramyxovirus polypeptides, parvovirus polypeptides, pestivirus polypeptides, picorna virus polypeptides, e.g., a poliovirus capsid polypeptide, pox virus polypeptides, e.g., a vaccina virus polypeptide, rabies virus polypeptides, e.g., a rabies virus glycoprotein G, reovirus polypeptides, retrovirus polypeptides, and rotavirus polypeptides.

Examples of bacterial antigenic and immunogenic polypeptides include, but are not limited to, *Actinomyces* polypeptides, *Bacillus* polypeptides, *Bacteroides* polypeptides, *Bordetella* polypeptides, *Bartonella* polypeptides, *Borrelia* polypeptides, e.g., *B. burgdorferi* OspA, *Brucella* polypeptides, *Campylobacter* polypeptides, *Capnocytophaga* polypeptides, *Chlamydia* polypeptides, *Clostridium* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides, e.g., H. influenzae type b outer membrane protein, *Helicobacter* polypeptides, *Klebsiella* polypeptides, L-form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides, *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, *Streptococcus* polypeptides, e.g., S. pyogenes M proteins, *Treponema* polypeptides, and *Yersinia* polypeptides, e.g., Y. pestis F1 and V antigens.

Examples of fungal immunogenic and antigenic polypeptides include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite immunogenic and antigenic polypeptides include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides, e.g., *P. falciparum* circumsporozoite (PfCSP), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of helminth parasite immunogenic and antigenic polypeptides include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides, *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides.

Examples of ectoparasite immunogenic and antigenic polypeptides include, but are not limited to, polypeptide (including protective antigens as well as allergens) from fleas; ticks, including hard ticks and soft ticks; flies, such as midges, mosquitos, sand flies, black flies, horse flies, horn flies, deer flies, tsetse flies, stable flies, myiasis-causing flies and biting gnats; ants; spiders, lice; mites; and true bugs, such as bed bugs and kissing bugs.

Examples of tumor-associated antigenic and immunogenic polypeptides include, but are not limited to, tumor-specific immunoglobulin variable regions, GM2, Tn, sTn, Thompson-Friedenreich antigen (TF), Globo H, Le (y), MUC 1, MUC2, MUC3, MUC4, MUCSAC, MUC5B, MUC7, carcinoembryonic antigens, beta chain of human chorionic gonadotropin (hCG beta), HER2/neu, PSMA, EGFRvIII, KSA, PSA, PSCA, GP100, MAGE 1, MAGE 2, TRP 1, TRP 2, tyrosinase, MART-1, PAP, CEA, BAGE, MAGE, RAGE, and related proteins.

Examples of allergens includes pollens, insect venoms, animal dander, dust, fungal spores, and drugs (e. g., penicillin). Examples of natural, animal, and plant allergens can be found in International Patent Application WO 98/18810.

In summary, the spores themselves can be used (as non-modified spores) as an adjuvant for immunomodulatory molecules or vaccines (e.g., genetic vaccines, DNA vaccines, protein vaccines, attenuated or killed viral vaccines). Furthermore, for use as adjuvants, any such spores can be viable or non-viable. As used herein, an "adjuvant" is a compound that acts in a non-specific manner to augment specific immunity (e.g., an immune response) to an immunomodulatory molecule, such as, for example, an immunogenic polypeptide or peptide or antigen, by stimulating an earlier, stronger or more prolonged response to an immunomodulatory molecule. By "adjuvant effect" is intended an augmentation or increase in immunity to an immunomodulatory molecule (e.g., an antigen).

REFERENCES

Banchereau J, Briere F, Caux C, Davoust J, Lebecque S, Liu Y J, Pulendran B, Palucka K. 2000. Immunobiology of dendritic cells. Ann Rev Immunol. 18:767-811.

Ben-Yedidia T, Abel L, Arnon R, Globerson A. 1998. Efficacy of anti-influenza peptide vaccine in aged mice. Mech Aging Dev. 104(1):11-23.

Bluestone J A. 1995. New perspectives of CD28-B7-mediated T cell costimulation. Immunity. 2(6):555-9.

Caruso A, Flamminio G, Folghera \S, Pernin L, Foresti I, Balsari A and Turano A. 1993. Expression of activation markers on peripheral blood lymphocytes following oral administration of *Bacillus subtilis* spores. Int. J. Immunopharmac. 15: 87-92.

Chambers C, 2001. The expanding world of co-stimulation: the two signal model revisited. TRENDS in Imunol. 22:217.

Chintalacharuvu S R, Nagy N U, Sigmund N, Nedrud J G, Amm M E, Emancipator S N. 2001. T cell cytokines determine the severity of experimental IgA nephropathy by regulating IgA glycosylation. Clin Exp Immunol. 126(2): 326-33.

Cipriandi G, Scordamaglia A, Ruffoni S, Pizzorno G and Canonica G W. 1986a. Effects of an adjunctive treatment with *Bacillus subtilis* for food allergy. Chemioterapia. 5: 408-410.

Ciprandi G, Scordamagalia A, Venuti D, Caria M and Canonica G. W. 1986b. In vitro effects of *bacilus subtilis* on the immune response. Chemoterapia. 5:404-407.

Cohn, F. 1872. "Untersuchungen uber Bakterien." Beitrage zur Biologie der Pflanzen, 1875 1 (Heft 2) 1:127-224.

Danengerg H D, Ben-Yehuda A, Zakay-Rones Z, Gross D J and Friedman G. 1997. Dehydroepiandrosterone treatment is not beneficial to the immune response to influenza in elderly subjects. J. Clin Endroclinol Metab. 82: 2911-2914.

Davenport F M, Hennesy A V and Askin F B. 1968. Lack of adjuvant effect of A1PO on purified influenza virus hemagglutinins in man. J Immunol. 100(5): 1139-40.

Ehrenberg, C. G. 1835. "Dritter Beitrag zur Erkenntniss grosser Organisation in der Richtung des kleinsten Raumes." Physikalische Abhandlungen der Koeniglichen Akademie der Wissenschaften zu Berlin aus den Jahren 1833-1835. pp. 143-336.

Fiorini G, Cimminiello C, Chianese R, Visconti G P, Cova D, Uberti T and Gibelli A. 1985. *Bacillus subtillis* selectively stimulates the synthesis of membrane bpoound and secreted IgA. Chemoteripia. 4: 310-312.

Fujihashi K, Toshiya K and mcGhee J R. 2000. Mucosal vacination and immune responses in the elderly. Vacine. 18: 1675-1680.

Glezen W P, Alpers M. 1999. Maternal immunization. Clin Infect Dis February; 28(2):219-24.

Green D H, Wakeley P R, Page A, Barnes A, Baccigalupi L, Ricca R and Cuttting S M. 1999. Characterization of Bacillus species used for oral bacteriotherapy and bacterioprophylaxis of gastrointestinal disorders. Appl. Environ. Microbiol. 65:4288.

Hoa N T, Baccigalupi L, Huxham A, Smertenko A, Van P H, Ammendola S, Rica E and Cutting S M. 2000. Characterization of Bacillus species used for oral bacteriotherapy and bacterioprophylaxis of gastrointestinal disorders. Appl. Environ. Microbiol. 66: 5241.

HoaTT, Duc L H, Isticato R, Baccigalupi L, Ricca E, Van P H and Cutting S. 2001. Fate and dissemination of *Bacillus subtilis* spores in a murine model. Appl. Environ. Microbiol. 66: 5241.

Hodge L M, Marinaro M, Jones H P, McGhee J R, Kiyono H, Simecka J W. 2001. Immunoglobulin A (IgA) responses and IgE-associated inflammation along the respiratory tract after mucosal but not systemic immunization. : Infect Immun April;69(4):2328-38.

Houba V, Berger F M, Dinarello C A, Johnson A G, Manuel J, Van der Meer J W, Philippeaux M M, Vilcek J and Vogels M T. 1992. Protodyne: an immunostimulatory protein component, prepared from gram-positive *Bacillus subtilis*. Dev. Biol. Stand. 77: 1211-128.

Hinmanen J -P, Pyhala L, Olander R-M, Merimska 0, Kuzina T, Lysyuk A, pronin A, Sanin A, Helander I M and Sarvas M. 1993. Biological activities of lipoteichoic acid and peptidoglycan-tichoic acid of *B. subtilis* 168 9Marburg). J. Gen. Microbiol. 139: 2659-2665.

Johnen H, Kulbe H and Pecher G. 2001. Long-term tumour growth suppression in mice immunized with naked DNA of the human tumour antigen mucin (MUC1). Cancer Immunol. Immunother. 50: 356-360.

Kalinski P, Hilkens C M, Wierenga E A, Kapsenberg M L 1999. T-cell priming by type-1 and type-2 polarized dendritic cells: the concept of a third signal.: Immunol Today December ; 20(12):561-7.

Langenkamp A, Messi M, Lanzavecchia A, Sallusto F. 2000. Kinetics of dendritic cell activation: impact on priming of TH1, TH2 and nonpolarized T cells. Nat Immunol. (4): 311-6.

Lyden T W, Robinson J M, Tridandapani S, Teillaud J L, Garber S A, Osborne J M, Frey J, Budde P, Anderson C L. 2001. The Fc receptor for IgG expressed in the villus endothelium of human placenta is Fc gamma RIIb2. J Immunol 166(6):3882-9.

Maidak B L, Cole J R, Lilburn T G, Parker C T Jr, Saxman P R, Stredwick J M, Garrity GM, Li B, Olsen G J, Pramanik S, Schmidt T M, Tiedje J M. 2000. The RDP (Ribosomal Database Project) continues. Nucleic Acids Res; 28(1): 173-4.

Malkiel S and Hargis B J. 1971. The adjuvant activity of *bacillus subtilis* and *subtiliis*. J. Allergy. Clin. Immunol. 48: 220-223.

Manning B M, Enioutina E Y, Visic D M, Knudsen A D and Daynes R A. 2001. CpG DNA functions as an effective adjuvant for the induction of immune responses in aged mice. Exp. Geront. 37: 107-126.

Mishell B. B. and Shiigi S. M. eds. 1980. Selected methods in cellular immunology. W. H. Freeman and Company, New York.

Mazza P. 1994. The use of *bacillus subtilis* as an anti-diarrhoeal microorganism. Boll. Chim. Farm. 133:3.

Morelli A E, Zahorchak A F, Larregina A T, Colvin B L, Logar A J, Takayama T, Falo L D, Thomson A W.2001. Cytokine production by mouse myeloid dendritic cells in relation to differentiation and terminal maturation induced by lipopolysaccharide or CD40 ligation Blood.;98(5): 1512-23.

Nagao A T, Friedlander-Del Nero D, Arslanian C, Carneiro-Sampaio M M. 2001. Elevated levels and different repertoire profile of colostral anti-LPS antibodies may have a significant role in compensating newborn immunity. Scand J Immunol 53(6):602-9.

Okoko J B, Wesumperuma H L, Hart C A. 2001. The influence of prematurity and low birthweight on transplacental antibody transfer in a rural West African population. Trop Med Int Health July 2001;6(7):529-34. Trop Med Int Health 6(7):529-34.

Parissi-Crivelli A, Parissi-Crivelli J M, Giron J A 2000. Recognition of enteropathogenic Escherichia coli virulence determinants by human colostrum and serum antibodies. J Clin Microbiol 38(7):2696-700.

Rappuoli R, Pizza M, Douce G and Dougan G. 1999. Structure and mucosal adjuvanticity of cholera and *Escherichia coli* heat-labile enterotoxins. 20:493.

Reis e Sousa C., Hieny S, Scharton-Kersten T, Jankovic D, Charest H, Germain R. N. aand Sher A. 1997. In vivo microbial stimulationinduces rapid CD40 ligand-independent production of Interleukin 12 by dendritic cells and their residtribution to T cell areas. J.Exp. Med. 186: 1819-1829.

Senesi S, Celandroni F, Tavanti A, and Ghelardi E. 2001. Molecular characterization and identification of *bacillus clausii* strains marketed for use in oral bacteriotheraphy. Appl. Environ. Microbiol. 67: 834.

Sneath, P. H. A. 1986. Endospore forming gram positive rods and cocci. Bergey's Manual of Systemic Bacteriology. (Ed. Holt J. G.) Williams and Wilkins. Baltimore. 2.

Spencer N F, Norton S D, Harrison L L, Li G Z and Daynes R A. 1996. Dysregulation of IL-10 production with aging: possible linkage to the age-asociated decline in DHEA and its sulphates derivative. Exp. Gerontol. 31: 393-408

Svensson M, Stockinger B, Wick M J. 1997. Bone marrow-derived dendritic cells can process bacteria for MHC-I and MHC-II presentation to T cells. J Immunol. 158(9):4229-36.

Tortorella C, Pisconti A, Piazzolla G and Antonaci S. 2002. APC-dependant impairment of T cell proliferation in aging: role of CD28- and IL-12/IL-15 mediated signaling. Mech. Aging Dev. 123: 1389-1392.

van Ginkel, F. W., R. J. Jackson, Y. Yuki, J. R. McGhee. 2000. The mucosal adjuvant cholera toxin redirects vaccine proteins into olfactory tissues. J. Immunol. 165:47.

What is claimed is:

1. A pharmaceutical composition for administration to a human or animal subject, the composition comprising spores of *Bacillus subtilis* strains which contain a 16SrRNA 99% similar at a genetic level to *Bacillus subtilis* strain 168 (ATCC Accession No. 23857), other than spores in which antigenic sequences have been cloned and expressed; and an antigenic component, the spores being present in an amount effective to stimulate or enhance immune responsiveness in the subject.

2. The pharmaceutical composition according to claim 1, in which the amount of the spores is effective to achieve an effect selected from the group consisting of (a) an adjuvant effect; (b) an immunomodulatory effect; (c) an immune potentiation effect; (d) a dendritic cell maturation effect; and (e) any combination of two or more of effects (a) to (d).

3. The pharmaceutical composition according to claim 1 or claim 2, wherein the spores are germination-deficient.

4. The pharmaceutical composition according to claim 1 or claim 2, wherein the composition comprises an admixture of the spores and the antigenic component.

5. The pharmaceutical composition according to claim 1 or claim 2, wherein the spores are coated with or linked to DNA via a non-recombinant linkage, whereby the spores function as a carrier for a DNA vaccine.

6. The pharmaceutical composition according to claim 1 or claim 2, wherein the antigenic component is a vaccine antigen, the spores being present in an amount effective to function as an adjuvant in association with the vaccine antigen.

7. The pharmaceutical composition according to claim 6, in which the vaccine antigen is specific for pathogens, tumors, allergens, toxins or venoms.

8. The pharmaceutical composition according to claim 1, wherein the amount of the spores is effective to enable the spores to function as a cell maturator or activator of antigen-presenting cells.

9. The pharmaceutical composition according to claim 1, wherein the amount of the spores is effective to enable the spores to function as a non-specific booster of innate and humoral immunity.

10. The pharmaceutical composition according to claim 1, wherein the amount of the spores is effective to enable the spores function as a booster of T-independent and T-dependent humoral immune responses.

11. The pharmaceutical composition according to claim 1, wherein the spores are present in the amount of from $10^5$ to $10_{10}$ spores per unit dose.

* * * * *